(12) United States Patent
Ueno et al.

(10) Patent No.: US 7,916,280 B2
(45) Date of Patent: Mar. 29, 2011

(54) BLOOD ANALYZER AND BLOOD ANALYZING METHOD FOR CLASSIFYING WHITE BLOOD CELLS

(75) Inventors: Kunio Ueno, Kakogawa (JP); Yuichi Hamada, Kobe (JP)

(73) Assignee: Sysmex Corporation, Kobe (JP)

( * ) Notice: Subject to any disclaimer, the term of this patent is extended or adjusted under 35 U.S.C. 154(b) by 123 days.

(21) Appl. No.: 11/599,910

(22) Filed: Nov. 15, 2006

(65) Prior Publication Data

US 2007/0109530 A1    May 17, 2007

(30) Foreign Application Priority Data

Nov. 15, 2005    (JP) .................................. 2005-329919

(51) Int. Cl.
*G01N 33/48* (2006.01)
(52) U.S. Cl. ......................................... 356/39; 356/339
(58) Field of Classification Search .................... 356/39, 356/246, 436, 337–339
See application file for complete search history.

(56) References Cited

U.S. PATENT DOCUMENTS

| 4,157,499 | A | * | 6/1979 | Kacerek ........................... 377/12 |
| 4,850,707 | A | | 7/1989 | Bowen et al. |
| 5,616,501 | A | | 4/1997 | Rodriguez et al. |
| 5,739,902 | A | | 4/1998 | Gjelsnes et al. |
| 5,805,281 | A | * | 9/1998 | Knowlton et al. ............ 356/336 |
| 6,004,816 | A | | 12/1999 | Mizukami et al. |
| 6,365,106 | B1 | | 4/2002 | Nagai |
| 6,525,807 | B1 | * | 2/2003 | Morikawa et al. .............. 356/72 |
| 7,105,355 | B2 | * | 9/2006 | Kurabayashi et al. ........ 436/165 |
| 2002/0080341 | A1 | | 6/2002 | Kosaka |
| 2005/0073686 | A1 | * | 4/2005 | Roth et al. ..................... 356/436 |
| 2005/0202400 | A1 | * | 9/2005 | Tsuji et al. ........................ 435/4 |

FOREIGN PATENT DOCUMENTS

| EP | 0529666 A2 | 3/1993 |
| EP | 1542008 A1 | 6/2005 |
| WO | WO 94/29695 A1 | 12/1994 |
| WO | WO 2005/017499 A2 | 2/2005 |

OTHER PUBLICATIONS

Hamamatsu, http://web.archive.org/web/20040827045013/http://sales.hamamatsu.com/en/products/solid-state-division/si-photodiode-series/si-apd.php, Aug. 27, 2004.*
European Search Report for corresponding European Application No. 06023539.7 dated Feb. 15, 2008.

* cited by examiner

*Primary Examiner* — Tarifur Chowdhury
*Assistant Examiner* — Michael LaPage
(74) *Attorney, Agent, or Firm* — Brinks Hofer Gilson & Lione

(57) ABSTRACT

The present invention provides a blood analyzer. The blood analyzer comprises a flow cell in which a first measurement sample flows, a light source for irradiating the first measurement sample flowing in the flow cell, a PIN photodiode for detecting a side scattered light from the first measurement sample irradiated by the light source, and an avalanche photodiode for detecting a side fluorescence light from the first measurement sample irradiated by the light source. The blood analyzer also comprises a signal processing part which has a low pass filter for reducing high frequency noise included in the side fluorescent light signal. A cut-off frequency of the low pass filter is set so that the blood analyzer can classify white blood cells in the first measurement sample into at least four groups comprising neutrophils, lymphocytes, monocytes, and eosinophils, based solely on the side scattered light signal and the side fluorescent light signal.

12 Claims, 23 Drawing Sheets

BLOOD ANALYZER AND BLOOD ANALYZING METHOD FOR CLASSIFYING WHITE BLOOD CELLS

This application claims priority under 35 U.S.C. §119 to Japanese Patent Application No. JP2005-329919 filed Nov. 15, 2005, the entire content of which is hereby incorporated by reference.

FIELD OF THE INVENTION

The present invention relates to a blood analyzer and method for analyzing blood sample.

BACKGROUND

A blood analyzer, which includes an optical flow cytometer, for analyzing a blood sample is known. The flow cytometer is provided with a flow cell for conducting the liquid of the blood sample, a light source for irradiating light onto the flow cell, and a light receiving element, and the light irradiated from the light source is scattered by the particles in the flow cell. The hemolyzing process of the red blood cells and the staining process of the particles of the white blood cells and the like are performed by adding hemolytic agent and fluorescence reagent to the blood sample, and the stained particles emit fluorescence light when receiving light. The scattered light and the fluorescence light are received by the light receiving elements, and the detection signals thereof are analyzed to measure the white blood cells in the blood sample and to classify the white blood cells to lymphocytes, monocytes, granulocytes and the like. In such flow cytometer, since the classification of the white blood cells and the ghosts (red blood cell membrane not completely shrunk with hemolytic agent) is discriminated using the fluorescent light signal, the hemolytic agent having high hemolyzing ability of shrinking the red blood cells to an extent the sizes of the white blood cells and the ghost can be clearly distinguished does not need to be used and thus the extent of damage of the white blood cells is alleviated and the form of the white blood cells is maintained. The reagent for dissolving the red blood cells while maintaining the form of the white blood cells to have the blood sample in a state suitable for the classification of the white blood cells has been disclosed (see U.S. Pat. No. 6,004, 816).

Furthermore, an optical system of high measurement accuracy becomes necessary since the classification of the white blood cells by means of the flow cytometer is performed based on the slight difference in size and form of the cell or the nucleus of each white blood cell. Moreover, the optical system of high measurement accuracy is necessary to discriminate the white blood cells and the ghosts using the fluorescent light signal since some ghosts are attached with a small amount of fluorescent pigment and thus emit fluorescent light signal. A photo-multiplier (photoelectron multiplier) having high sensitivity is generally used as the fluorescent light receiving element (see e.g., U.S. Pat. No. 6,365,106). Furthermore, a flow cytometer using an avalanche photodiode (APD) as the light receiving element for receiving fluorescence light is also disclosed (see U.S. Pat. No. 5,739,902).

The amplification ratio of the signal of the element itself is low in the avalanche photodiode compared to the photo-multiplier, and thus the gain of the amplifying circuit arranged in the post-stage of the element must be set large. However, if the output signal of the avalanche photodiode is amplified with the amplifying circuit set with a large gain, the level of high frequency noise generated in the amplifying circuit increases, and high precision analysis of the sample becomes difficult.

BRIEF SUMMARY

The scope of the present invention is defined solely by the appended claims, and is not affected to any degree by the statements within this summary.

A first aspect of the present invention is a blood analyzer, comprising: a sample preparing part for preparing a measurement sample comprising a blood, a hemolyzing reagent, and a staining reagent; a flow cell in which the measurement sample flows; a light source for irradiating the measurement sample flowing in the flow cell; a scattered light detector for detecting scattered light from the measurement sample irradiated by the light source; a fluorescence light detector comprising an avalanche photo diode for detecting fluorescence light from the measurement sample irradiated by the light source; a signal processing part for processing a first detection signal from the scattered light detector and a second detection signal from the fluorescence light detector, wherein the signal processing part reduces high frequency noise included in an amplified second detection signal; and a analysis part for classifying white blood cells in the blood into groups based on the first and the second detection signals processed by the signal processing part.

A second aspect of the present invention is a blood analyzer, comprising: a sample preparing part for preparing a measurement sample comprising a blood, a hemolyzing reagent, and a staining reagent; a flow cell in which the measurement sample flows; a light source for irradiating the measurement sample flowing in the flow cell; a scattered light detector for detecting scattered light from the measurement sample irradiated by the light source; a fluorescence light detector comprising an avalanche photo diode for detecting fluorescence light from the measurement sample irradiated by the light source; a signal processing part for processing a first detection signal from the scattered light detector and a second detection signal from the fluorescence light detector, wherein the signal processing part comprises a low pass filter for reducing high frequency noise included in an amplified second detection signal; and a analysis part for classifying white blood cells in the blood into groups based on the first and the second detection signals processed by the signal processing part; wherein a cutoff frequency of the low pass filter is less than frequency Y of following formula:

$$Y = 17.289 \text{EXP}(-0.022C) + 2$$

(C represents electric capacity between terminals of the avalanche photo diode).

A third aspect of the present invention is a blood analyzing method, comprising: preparing a measurement sample comprising a blood, a hemolyzing reagent, and a staining reagent; exposing the measurement sample to light from a light source; detecting scattered light from the measurement sample irradiated by the light source; detecting, by an avalanche photo diode, fluorescence light from the measurement sample irradiated by the light source; processing a first detection signal obtained from the scattered light; processing a second detection signal obtained from the fluorescence light, the processing of the second detection signal comprising reducing high frequency noise included in an amplified second detection signal; and classifying white blood cells in the blood into groups based on a processed first detection signal and a processed second detection signal.

BRIEF DESCRIPTION OF THE DRAWINGS

The invention, together with objects and advantages thereof, may best be understood by reference to the following description of the presently preferred embodiments together with the accompanying drawings in which.

DETAILED DESCRIPTION OF THE PREFERRED EMBODIMENTS

The preferred embodiments of the present invention are described hereinafter with reference to the drawings.

Figure 1:
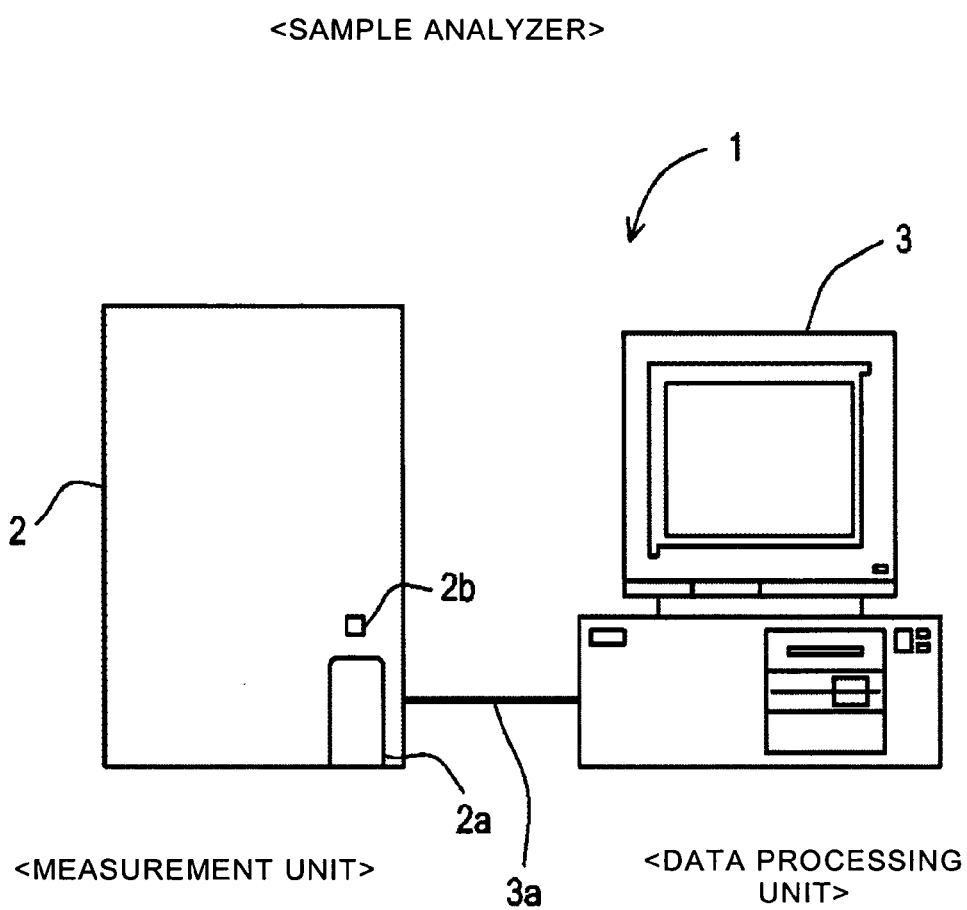
FIG. 1 is a front view briefly showing the structure of the sample analyzer of an embodiment.

FIG. 1 is a front view briefly showing the structure of the sample analyzer of an embodiment. As shown in FIG. 1, a sample analyzer 1 of the present embodiment is used in blood testings, comprises a measurement unit 2 and data processing unit 3. The measurement unit 2 performs predetermined measurements of components contained in blood specimens, and the measurement data are subjected to an analysis process when received by the data processing unit 3. The sample analyzer 1 is installed in medical facilities such as hospitals, or pathology laboratories and the like. The measurement unit 2 and data processing unit 3 are connected by a data transfer cable 3a so as to be capable of mutual data communications. The configuration is not limited to a direct connection between the measurement unit 1 and data processing unit 3 by the data transfer cable 3a, inasmuch as, for example, the measurement unit 2 and data processing unit 3 may also be connected through a dedicated line using a telephone line, or a communication network such as a LAN, Internet or the like.

Figure 2:
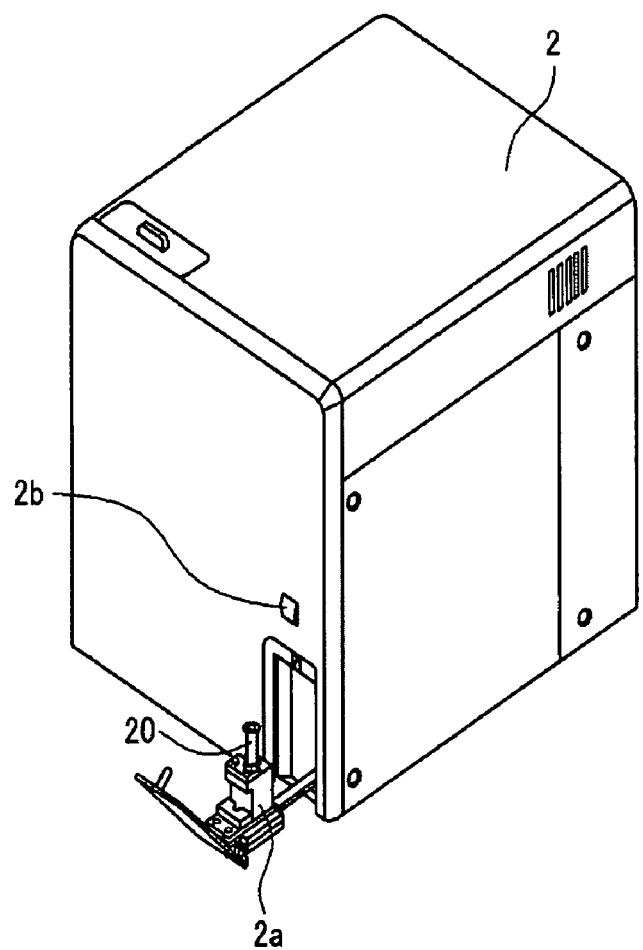
FIG. 2 is a perspective exterior view of the measurement unit provided in the sample analyzer of the embodiment.

FIG. 2 is a perspective view of the exterior of the measurement unit 2. As shown in FIG. 2, at the lower right of the front of the measurement unit 2, is provided with a blood collection tube placement unit 2a for placing a blood collection tube 20 that contains a blood sample. The blood collection tube placement unit 2a can receive a blood collection tube 20 placed therein by a user when a button switch 2b provided nearby is pressed by the user and the blood collection tube placement unit 2a moves in a forward direction. After the blood collection tube 20 has been placed, the user again presses the button switch 2b and the blood collection tube placement unit 2a withdraws and closes.

Figure 3:
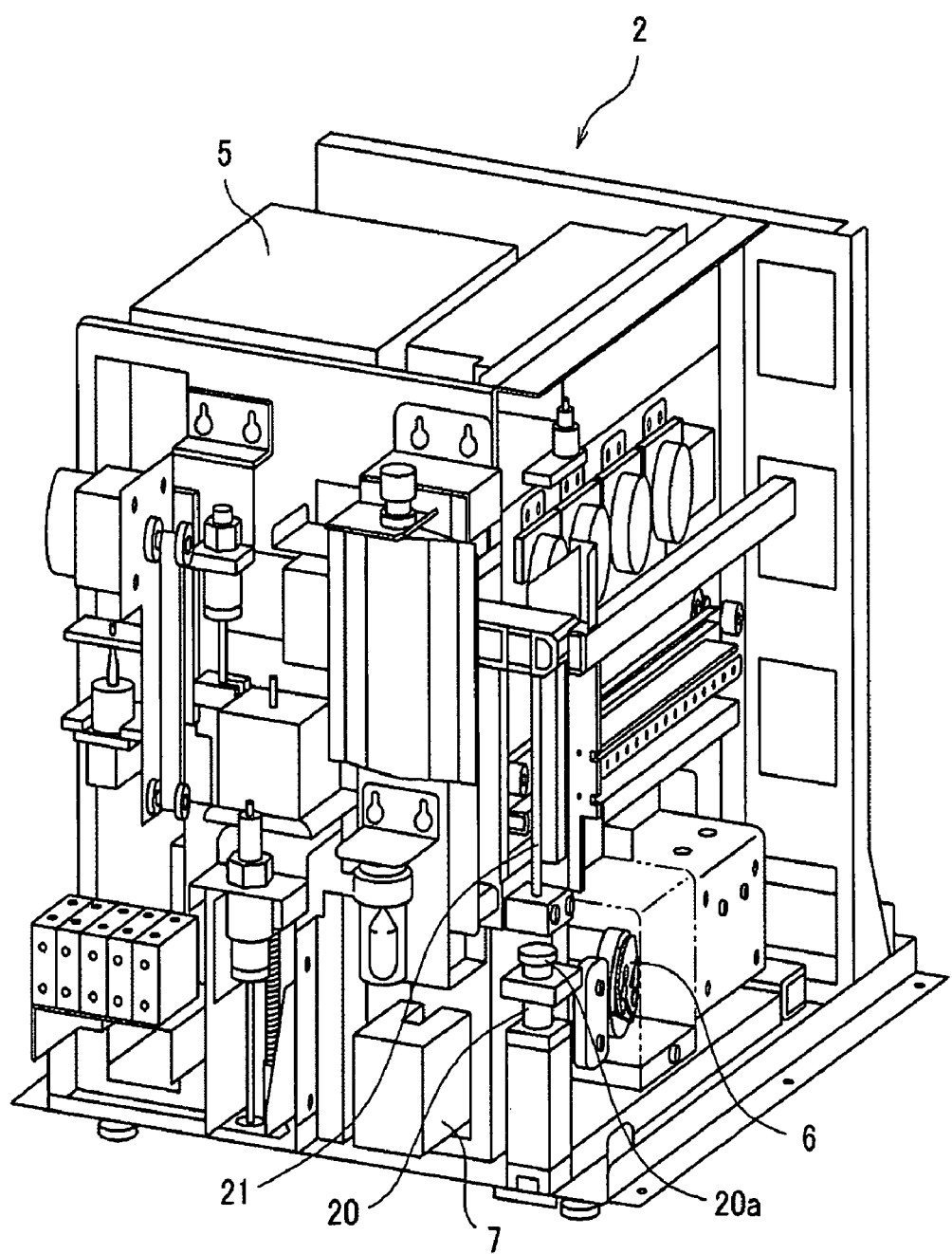
FIG. 3 is a perspective view showing the internal structure of the measurement unit provided in the sample analyzer of the embodiment.
Figure 4:
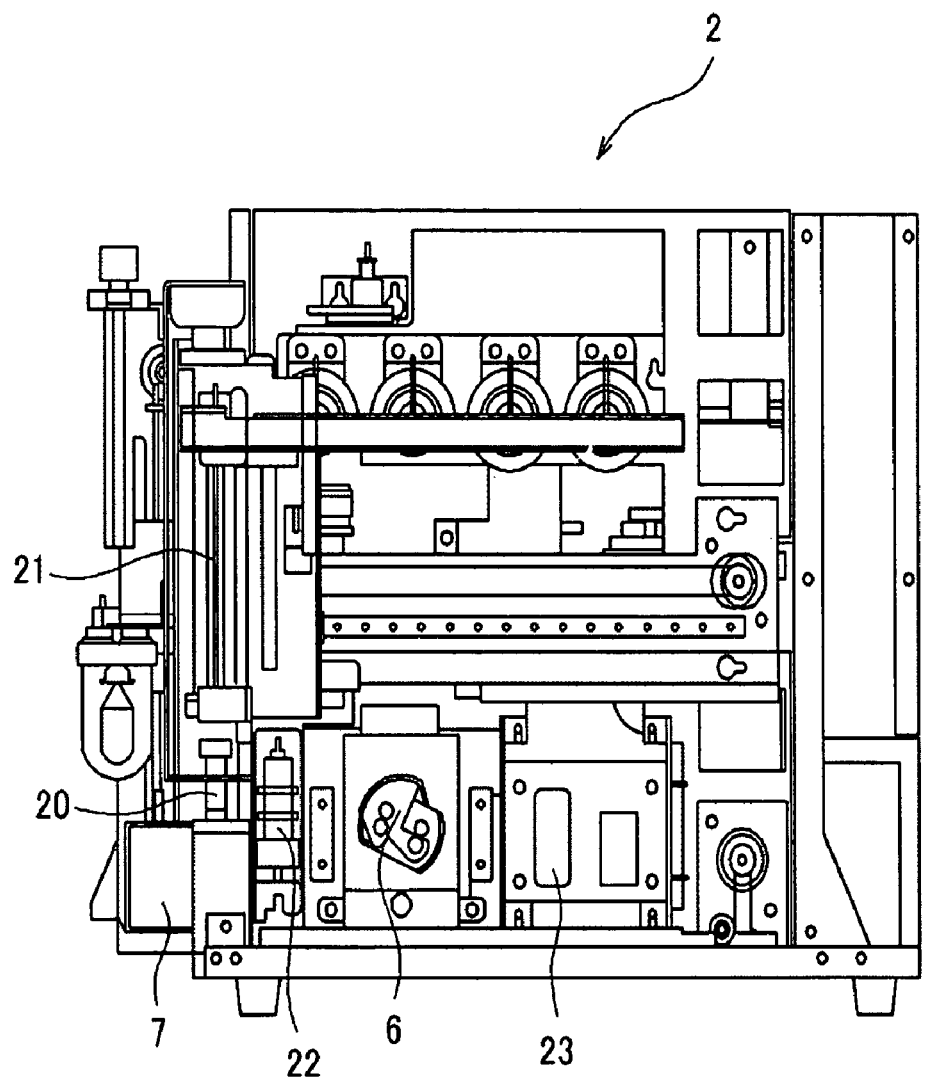
FIG. 4 is a side view showing the internal structure of the measurement unit provided in the sample analyzer of the embodiment.

FIG. 3 is a perspective view showing the interior structure of the measurement unit 2, and FIG. 4 is a side view of the same. The blood collection tube placement unit 2a holding the collection tube 20 is received within the measurement unit 2 as previously described, and the collection tube 20 is positioned at a predetermined suction position. A sample supply unit 4 including a pipette 21 for suctioning samples, chambers 22 and 23 for mixing and adjusting blood and reagent and the like is provided within the measurement unit 2. The pipette 21 is tube-like and extends vertically, and the tip is sharply tapered. The pipette 21 is linked to a syringe pump not shown in the drawing, and a predetermined amount of liquid can be suctioned or discharged by the operation of this syringe pump; the pipette 21 is also linked to a moving mechanism so as to be movable in vertical directions and forward and backward directions. The blood collection tube 20 is sealed by a rubber cap 20a, and the sharp tip of the pipette 21 pieces the cap 20a of the collection tube 20 placed at the suction position, and a predetermined amount of blood sample contained in the collection tube 20 can be suctioned by the pipette 21. As shown in FIG. 4, chambers 22 and 23 are provided behind the collection tube placement unit 2a; the pipette 21 is moved by the moving mechanism when the blood sample has been suctioned, and supplies the blood sample to the chambers 22 and 23 by discharging the blood sample into the chambers 22 and 23.

Figure 5:
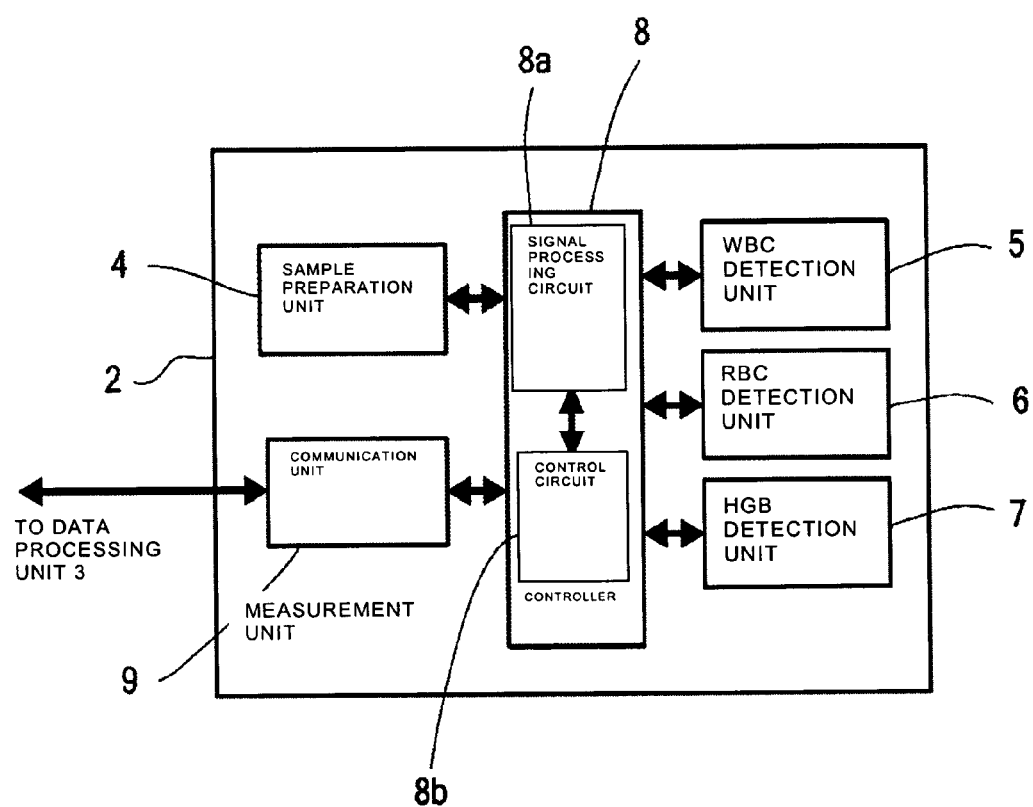
FIG. 5 is a block diagram showing the structure of the measurement unit provided in the sample analyzer of the embodiment.
Figure 6:
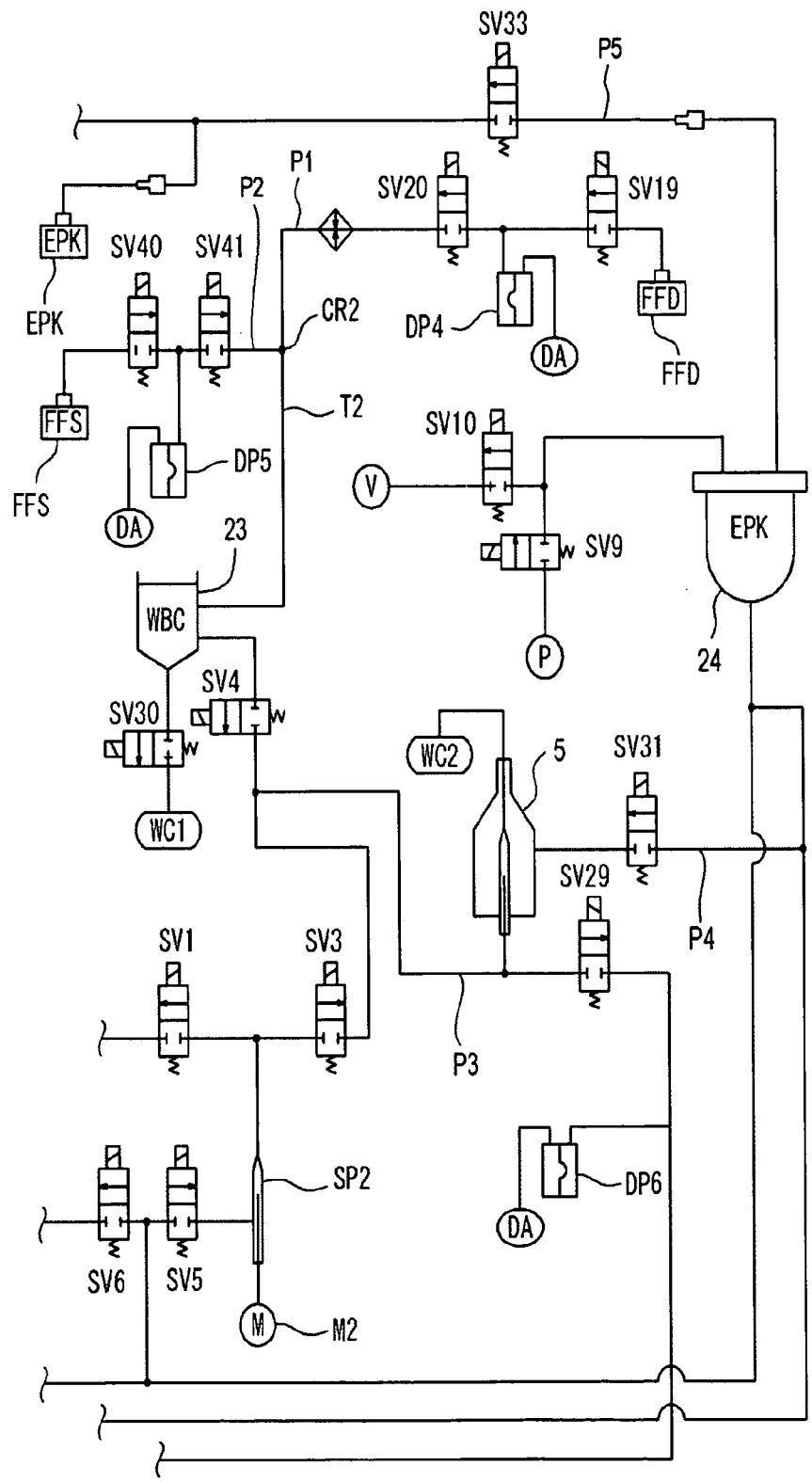
FIG. 6 is a fluid circuit diagram showing the structure of the sample supply section provided in the measurement unit.

FIG. 5 is a block diagram showing the structure of the measurement unit 2, and FIG. 6 is a flow circuit diagram showing the structure of the sample supply unit 4. As shown in FIG. 4, the measurement unit 2 is provided with a sample supply unit 4, WBC detection unit 5, RBC detection unit 6, HGB detection unit 7, control unit 8, and communication unit 9. The control unit 8 is configured by a CPU, ROM, RAM and the like, and performs operation control of each type of structural element of the measurement unit 2. The communication unit 9 is an interface, such as, for example, an RS-232C interface, USB interface, Ethernet (registered trademark), and is capable of sending and receiving data to/from the data processing unit 3.

As shown in FIG. 6, the sample supply unit 4 is a flow unit provided with a plurality of electromagnetic valves, diaphragm pumps and the like. Chamber 22 is used to prepare the sample supplied for the measurement of red blood cells and platelets, and the measurement of hemoglobin. The chamber 23 is used to prepare the sample supplied for white blood cell measurement. FIG. 6 shows only the structure of the flow circuit on the periphery of the chamber 23 in order to simplify the drawing. The chamber 23 is connected to a reagent container FFD accommodating hemolytic agent and a reagent container FFS accommodating staining fluid through fluid flow paths P1 and P2, such as tubes or the like. Electromagnetic valves SV19 and SV20 are provided in the fluid flow path P1 connecting the chamber 23 and the reagent container FFD, and a diaphragm pump DP4 is provided between the electromagnetic valves SV19 and SV20. The diaphragm pump DP4 is connected to a positive pressure source and a negative pressure source, such that the diaphragm pump DP4 can be operated by positive pressure drive and negative pressure drive. Electromagnetic valves SV40 and SV41 are provided in the fluid flow path P2 connecting the chamber 23 and the reagent container FFS, and a diaphragm pump DP5 is provided between the electromagnetic valves SV40 and SV41.

The electromagnetic valves SV19, SV20, SV40, SV41, and diaphragm pumps DP4 and DP5 are operationally controlled as follows, and are capable of supplying hemolytic agent and staining fluid to the chamber 23. First, the electromagnetic valve SV19, which is disposed on the reagent container FFD side of the diaphragm pump DP4, is opened, and with the electromagnetic valve SV20, which is disposed on the chamber 23 side of the diaphragm pump DP4, in the closed state, a hemolytic agent is supplied in a fixed dosage from the reagent container FFD by negative pressure actuation of the diaphragm pump DP4. Thereafter, the electromagnetic valve SV19 is closed, the electromagnetic valve SV20 is opened, and the fixed quantity of hemolytic agent is supplied to the chamber 23 by positive pressure actuation of the diaphragm pump DP4. Similarly, the electromagnetic valve SV40, which is disposed on the reagent container FFS side of the diaphragm pump DP5, is opened, and with the electromagnetic valve SV41, which is disposed on the chamber 23 side of the diaphragm pump DP5, in the closed state, a staining fluid is supplied in a fixed dosage from the reagent container FFS by negative pressure actuation of the diaphragm pump DP5. Thereafter, the electromagnetic valve SV40 is closed, the electromagnetic valve SV41 is opened, and the fixed quantity of staining fluid is supplied to the chamber 23 by positive pressure actuation of the diaphragm pump DP5. Thus, the blood sample and reagents (hemolytic reagent and staining fluid) are mixed and the sample is prepared for white blood cell measurement.

Furthermore, the chamber 23 is connected to the WBC detection unit flow cytometer through a fluid flow path P3 that includes tubes and an electromagnetic valve SV4. The fluid flow path P3 branches in its medial region, and electromagnetic valves SV1 and SV3 are connected in series at the branch. A syringe pump SP2 is disposed medially to the electromagnetic valves SV1 and SV3. A stepping motor M2 is connected to the syringe pump SP2, such that the syringe pump SP2 is actuated by the operation of the stepping motor M2. Furthermore, the fluid flow path P3 connecting the chamber 23 and the WBC detection unit 5 also branches, and an electromagnetic valve SV29 and diaphragm pump DP6 are connected at the branch. When white blood cells are measured by the WBC detection unit 5, the diaphragm pump DP6 is operated under negative pressure with the electromagnetic valves SV4 and SV29 in an open state, and the sample charges the fluid flow path P3 when the sample is suctioned from the chamber 23. When the sample charging is completed, the electromagnetic valves SV4 and SV29 are closed. Thereafter, the electromagnetic valve SV3 is opened, and the charged sample is supplied to the WBC detection unit 5 by operating the syringe pump SP2.

As shown in FIG. 6, the sample supply unit 4 is provided with a sheath fluid chamber 24, and the sheath fluid chamber 24 is connected to the WBC detection unit 5 through the fluid flow path P4. An electromagnetic valve SV31 is provided in the fluid flow path P4. The sheath fluid chamber 24 is a chamber for storing sheath fluid to be supplied to the WBC detection unit 5, and is connected to the sheath fluid container EPK that holds the sheath fluid through the fluid flow path P5 that includes tubes and an electromagnetic valve SV33. Before starting the measurement of white blood cells, the electromagnetic valve SV33 is opened and sheath fluid is supplied to the sheath fluid chamber 24, such that sheath fluid is stored in the sheath fluid chamber 24 beforehand. Then, when the measurement of white blood cells begins, the electromagnetic valve SV31 is opened, and sheath fluid stored in the sheath fluid chamber 24 is supplied to the WBC detection unit 5 simultaneously with the sample supplied to the WBC detection unit 5.

Figure 7:
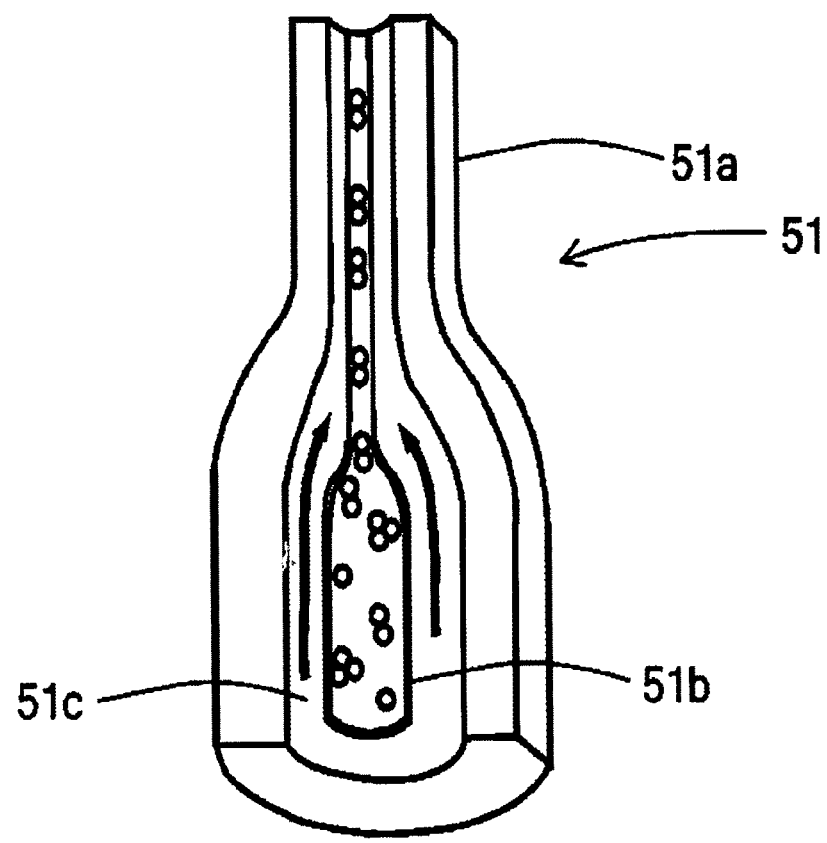
FIG. 7 is a perspective view schematically showing the structure of the flow cell provided in the measurement unit.

The WBC detection unit 5 is an optical type flow cytometer, and is capable of measuring white blood cells by a flow cytometry via a semiconductor laser. The WBC detection unit 5 is provided with a flow cell 51, which forms the fluid flow of the sample. FIG. 7 is a perspective view schematically showing the structure of the flow cell 51. The flow cell 51 is configured by a material such as transparent glass, glass, synthetic resin and the like, formed in a tube-like shape, and is a flow path through the interior of which the sheath fluid flows. The flow cell 51 is provided with an orifice 51a, the internal cavity of which has an aperture that is narrower than the other parts. The vicinity of the inlet of the orifice 51a of the flow cell 51 has a double-tube structure, and the internal side of this tube part becomes a sample nozzle 51b. The sample nozzle 51b is connected to the fluid flow path P3 of the sample supply unit 4, and sample is discharged through the sample nozzle 51b. Furthermore, the cavity on the outer side of the sample nozzle 51b is the flow path 51c through which the sheath fluid flows, and the flow path 51c is connected to the previously described fluid flow path P4. The sheath fluid supplied from the sheath fluid chamber 24 flows through the flow path 51c via the fluid flow path P4, and is introduced to the orifice 51a. The sheath fluid supplied to the flow cell 51 in this way flows so as to encapsulate the sample discharged from the sample nozzle 51b. Then, the sample flow is constricted by the orifice 51a, such that the particles of white blood cells and red blood cells contained in the sample are encapsulated in the sheath fluid and pass through the orifice 51a one by one.

Figure 8:
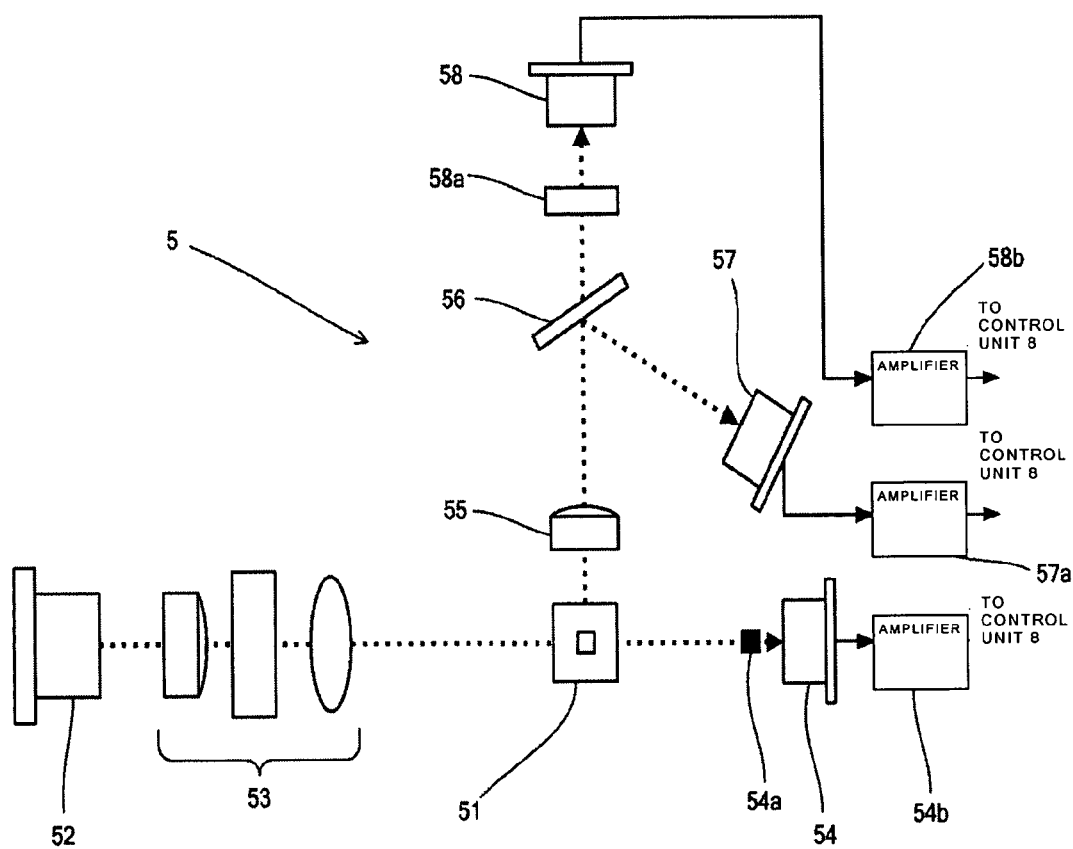
FIG. 8 is a brief plan view schematically showing the structure of the flow cytometer provided in the measurement unit.

FIG. 8 is a brief plan view that schematically shows the structure of the WBC detection unit 5. A semiconductor laser light source 52 is arranged in the WBC detection unit 5 so as to emit laser light toward the flow cell 51. An illumination lens system 53 including a plurality of lenses is arranged medially to the flow cell 51 and the semiconductor laser light source 52. Parallel beams emitted from the semiconductor laser light source 52 are collected at a beam spot by the illumination lens system 53. Furthermore, a beam stopper 54a is provided on the optical axis extending linearly from the semiconductor laser light source 52 so as to be opposite the illumination lens system 53 and with the flow cell 51 interposed therebetween. A photodiode 54 is arranged on the optical axis downstream of the beam stopper 54a.

When the sample flows through the flow cell 51, optical signals of scattered light and fluorescent light are generated by the laser light. Among these, the forward scattered light signals irradiate toward the photodiode 54. Among the light advancing along the optical axis extending linearly from the semiconductor laser 52, the direct light of the semiconductor laser 52 is blocked by the beam stopper 54a, and only the scattered light (hereinafter referred to as "forward scattered light") advancing along the optical axis direction enters the photodiode 54. The forward scattered light emitted from the flow cell 51 is subjected to photoelectric conversion by the photodiode 54, and the electrical signals (hereinafter referred to as "forward scattered light signals") generated by this conversion are amplified by an amplifier 54b, and output to the control unit 8. The forward scattered light signals reflect the size of the blood cells, and the size of the blood cells and the like can be obtained when the control unit 8 subjects the forward scattered light signals to signal processing.

Furthermore, a side collective lens 55 is arranged at the side of the flow cell 51, in a direction perpendicular to the optical axis extending linearly from the semiconductor laser light source 52 to the photodiode 54, and the lateral light (light emitted in a direction intersecting the optical axis) generated when the semiconductor laser irradiates the blood cells passing through the flow cell 51 is collected by the side collective lens 55. A dichroic mirror 56 is provided on the downstream side of the side collective lens 55, and the signal light transmitted from the side collective lens 55 is divided into a scattered light component and fluorescent light component by the dichroic mirror 56. A side scattered light photoreceptor photodiode 57 is provided at the side (the direction intersecting the direction of the optical axis connecting the side collective lens 55 and the dichroic mirror 56) of the dichroic mirror 56, and an optical filter 58a and avalanche photodiode 58 are provided on the optical axis on the downstream side of the dichroic mirror 56. Then, the side scattered light component separated by the dichroic mirror 56 is subjected to photoelectric conversion by the photodiode 57, and the electrical signals (hereinafter referred to as "side scattered light signals") generated by this conversion are amplified by an amplifier 57a and output to the control unit 8. The side scattered light signals reflect the internal information (size of the nucleus and the like) of the blood cells, and the size of the nucleus of the blood cell and the like can be obtained when the control unit 8 subjects the side scattered light signal to signal processing. Furthermore, the side fluorescent light component emitted from the dichroic mirror 56 is subjected to wavelength selection by the optical filter 58a, and subsequent photoelectric conversion by the avalanche photodiode 58, and the electrical signals (side fluorescent light signals) thus obtained are amplified by an amplifier 58b and output to the control unit 8. The side fluorescent light signals reflect information related to the degree of staining of the blood cells, and the stainability of the blood cells can be obtained by subjecting the side fluorescent light signals to signal processing.

The RBC detection unit 6 can measure the number of red blood cells and platelets by a sheath flow DC detection method. The RBC detection unit 6 has a flow cell, and sample is supplied from the previously mentioned chamber 22 to the flow cell. When measuring red blood cells and platelets, a sample is prepared by mixing solution fluid with the blood in the chamber 22. The sample is supplied from the sample supply unit to the flow cell together with the sheath fluid, and a flow is formed in which the sample is encapsulated in the sheath fluid within the flow cell. Furthermore, an aperture with an electrode is provided in the flow path in the flow cell, and the direct current (DC) resistance in the aperture is detected when the blood cells in the sample pass thought the aperture one by one, and the electrical signal of the DC resistance is output to the control unit 8. since the DC resistance increases when the blood cell passes through the aperture, the electrical signal reflects information of the passage of the blood cell through the aperture, and the red blood cells and platelets can be counted by subjecting the electrical signals to signal processing.

The HGB detection unit 7 is capable of measuring the amount of hemoglobin by the SLS hemoglobin method. The HGB detection unit 7 is provided with a cell for accommodating dilute sample, sample is supplied from the chamber 22 to this cell. When measuring hemoglobin, a sample is prepared by mixing dilution liquid and hemolytic reagent in blood in the chamber 22. The hemolytic reagent has the characteristic of transforming hemoglobin in the blood to SLS hemoglobin. Furthermore, a light-emitting diode and photodiode are arranged in opposition with the cell interposed therebetween, and light emitted from the light-emitting diode is received by the photodiode. The light-emitting diode emits light of a wavelength that has high absorption by SLS hemoglobin, and the cell is formed of a plastic material of high transparency. Thus, in the photodiode, only the transmission light absorbed by the dilute sample is received among the light emitted by the light-emitting diode. The photodiode outputs electrical signals corresponding to the amount of received light (optical density) to the control unit 8, and the control unit 8 compares this optical density with the optical density of the dilution liquid alone which was measured beforehand, then calculates the hemoglobin value.

The control unit 8 receives electrical signals from the WBC detection unit 5, the RBC detection unit 6, and the HGB detection unit 7, and obtains the measurement data indicating the size of the blood cells, the size of the nucleus of the blood cells, the stainability of the blood cells, the number of red blood cells, the number of blood platelets, the hemoglobin value and the like. As shown in FIG. 5, the control unit 8 includes a signal processing circuit 8a and a control circuit 8b, where the output signal (side fluorescent light signal, forward scattered light signal, side scattered light signal) of the WBC detection unit 5, the output signal of the RBC detection unit 6, and the output signal of the HGB detection unit 7 are respectively signal processed by the signal processing circuit 8a to acquire the measurement data, and the measurement data is transmitted to the data processing unit 3 by the control circuit 8b.

The data processing unit 3 is configured by a computer provided with a CPU, ROM, RAM, hard disk, communication interface, input unit including a keyboard and mouse and the like, and a display device. The communication interface is, for example, an RS-232C interface, USB interface, Ethernet (registered trademark), and is capable of sending and receiving data to/from the measurement unit 2. Furthermore, an operating system, and application program for analyzing the measurement data received from the measurement unit 2 are installed on the hard disk of the data processing unit 3. In the data processing unit 3, measurement data are analyzed, white blood cell count (WBC), red blood cell count (RBC), hemoglobin amount (HGB), hematocrit value (HCT, mean red blood cell volume (MCV), mean red blood cell hemoglobin (MCH), mean red blood cell hemoglobin concentration (MCHC), platelet count (PLT), are calculated, and a scattergram is prepared using the side scattered light signals and side fluorescent light signals, and the white blood cells are classifies as neutrophils, lymphocytes, monocytes, eosinophils, and basophils when the CPU executes the application program.

Figure 9:
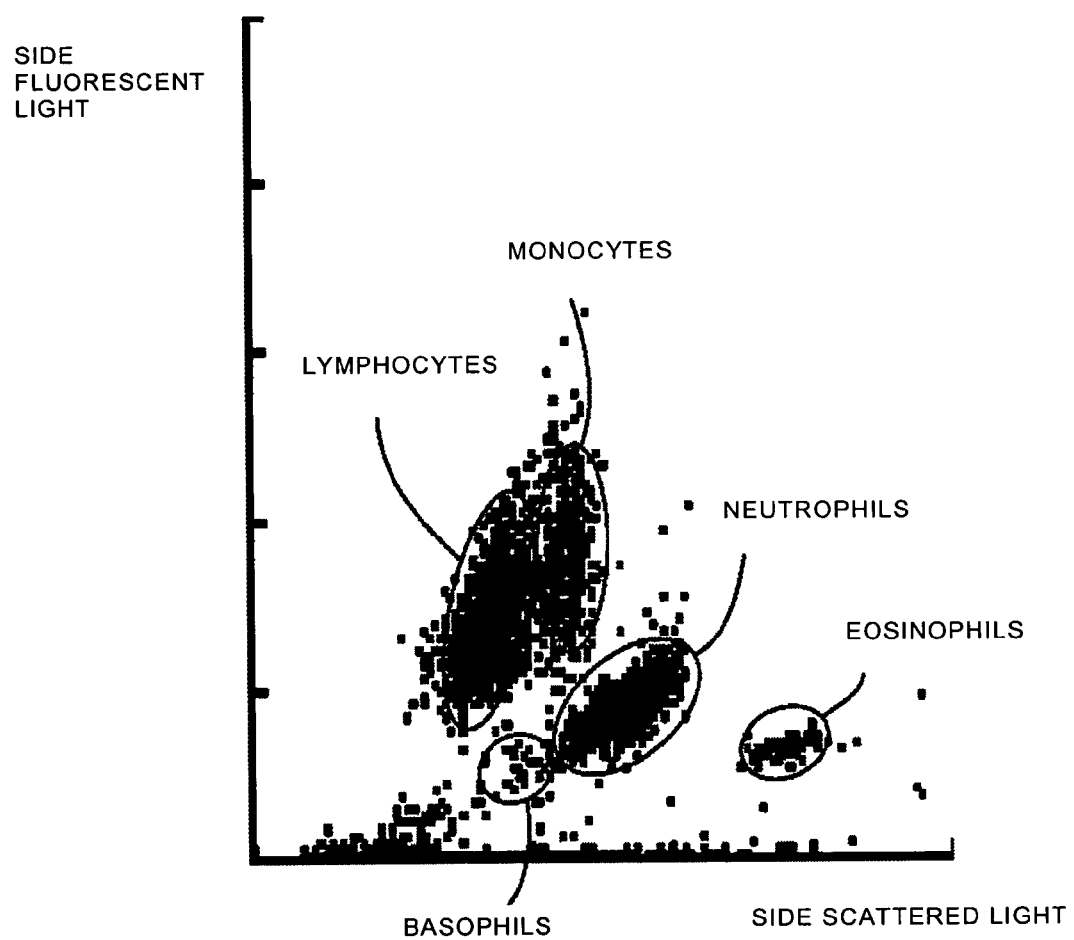
FIG. 9 is a scattergram prepared using the blood analyzer according to the embodiment.

FIG. 9 is a scattergram prepared using the blood analyzer according to the present embodiment. In FIG. 9, the vertical axis shows the intensity of the side fluorescent light (level of received light), and the horizontal axis shows the intensity of the side scattered light (level of received light). In the present experiment, measurement is performed using the same normal blood sample. The blood analyzer 1 according to the present embodiment has a configuration of classifying the white blood cells into five classification of neutrophils, lymphocytes, monocytes, eosinophils, and basophils all at once, where each cluster of neutrophils, lymphocytes, monocytes, eosinophils, and basophils is clearly formed in the scattergram prepared by the blood analyzer 1, as shown in FIG. 9, indicating that the white blood cells are classified at high precision.

Figure 10:
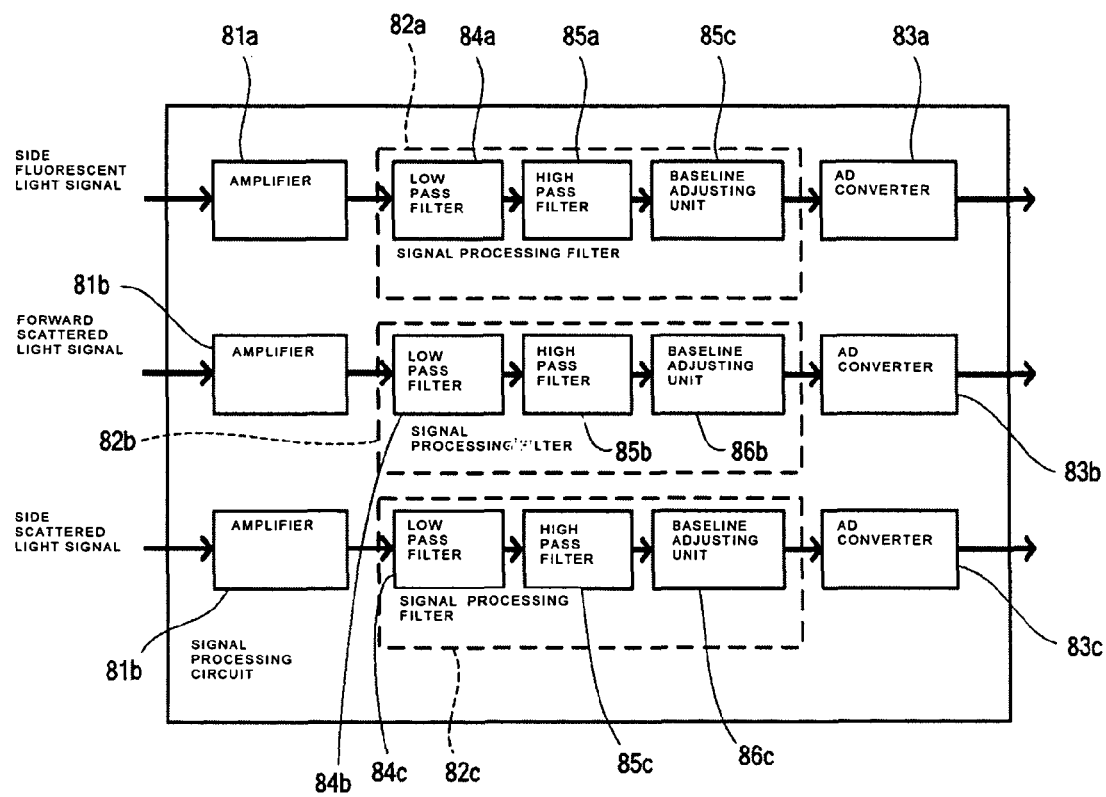
FIG. 10 is a block diagram showing a schematic configuration of the signal processing circuit shown in FIG. 5.

The configuration of the signal processing circuit 8a of the control unit 8 will now be further described in detail. FIG. 10 is a block diagram showing a schematic configuration of the signal processing circuit 8a shown in FIG. 5. As shown in FIG. 10, the signal processing circuit 8a includes amplifiers 81a to 81c, signal processing filters 82a to 82c, and AD converters 83a to 83c. The signal processing filters 82a to 82c respectively includes low pass filters (high cut filters) 84a to 84c for reducing the high frequency noise, high pass filters 85a to 85c for reducing the fluctuation at the baseline of the signal, and baseline adjusting units 86a to 86c for adjusting the baseline of the signal to a predetermined level. The side fluorescent light signal output from the WBC detection unit 5 is processed by the amplifier 81a, the signal processing filter 82a, and the AD converter 83a; the forward fluorescent light signal output from the WBC detection unit 5 is processed by the amplifier 81b, the signal processing filter 82b, and the AD converter 83b; and the side scattered light signal output from the WBC detection unit 5 is processed by the amplifier 81c, the signal processing filter 82c, and the AD converter 83c. Only the circuits for processing the output signals from the WBC detection unit 5 are shown in FIG. 10 to simplify the explanation, but circuits for processing the output signals of the RBC detection unit 6 and the HGB detection unit are also arranged in the signal processing circuit 8a.

The set value of gain of the amplifiers 81a to 81c is switched by the measurement mode (white blood cell classifying mode, reticular red blood cell measurement mode etc.) The gain adjustment is performed by adjusting the gain so that the standard particles appear at the appropriate appearing position when the standard particles (e.g., control blood, calibrator), whose appearing position on the scattergram is known in advance in an appropriately gain adjusted state, are being measured. The low pass filters 84a to 84c are set with an appropriate high pass cut-off frequency so as to efficiently attenuate the noise of the side fluorescent light signal, the forward scattered light signal, and the side scattered light signal. For example, the high pass cut-off frequency of the low pass filter 84a is set to less than or equal to the frequency Y obtained by equation (5).

$$Y = 10.482 EXP(-0.018C) + 1.3 \quad \text{(eq.5)}$$

C: inter-terminal capacity of avalanche photodiode

Figure 11:
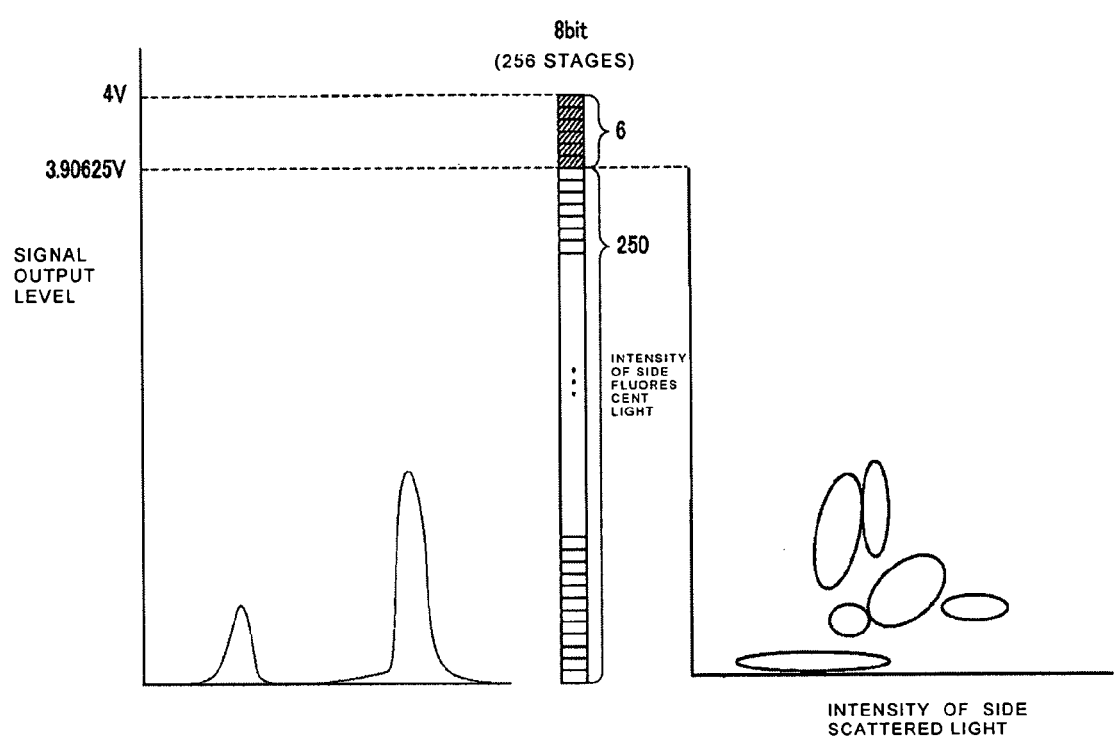
FIG. 11 is a frame format view explaining the range used in the analysis of the amplified signal of the side fluorescent light signal.
Figure 12:
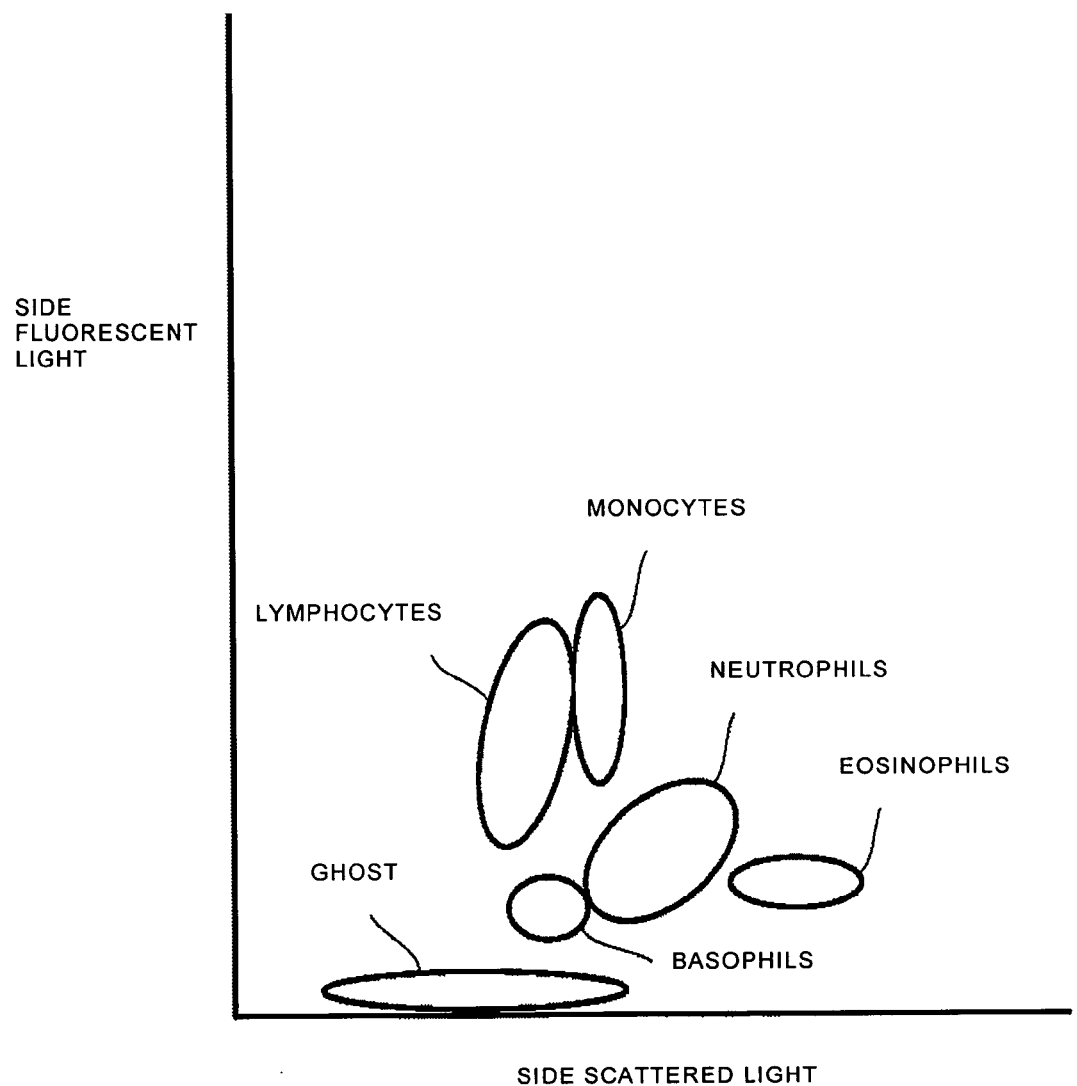
FIG. 12 is a scattergram obtained when the maximum allowable level of noise is set to 80 mVp-p.
Figure 13:
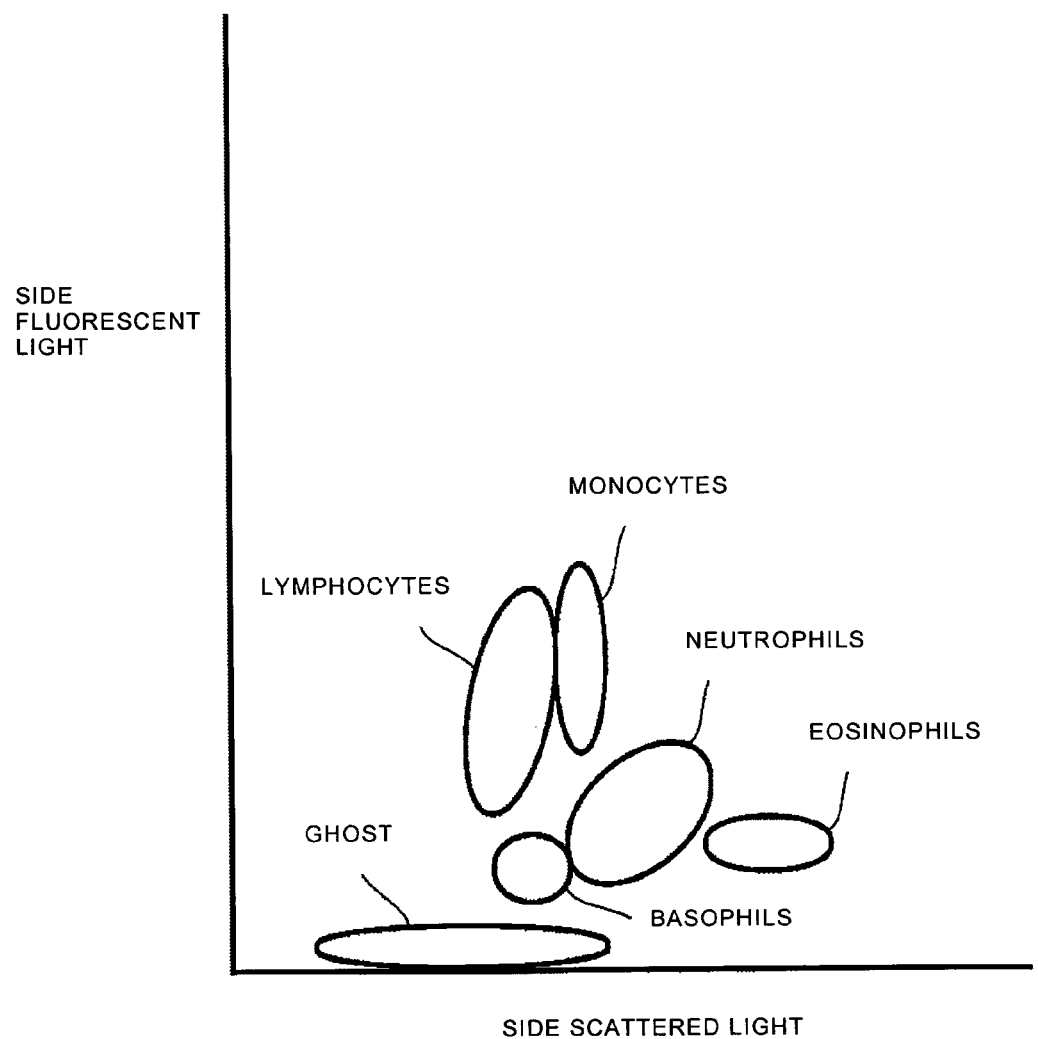
FIG. 13 is a scattergram obtained when the maximum allowable level of noise is set to 100 mVp-p.
Figure 14:
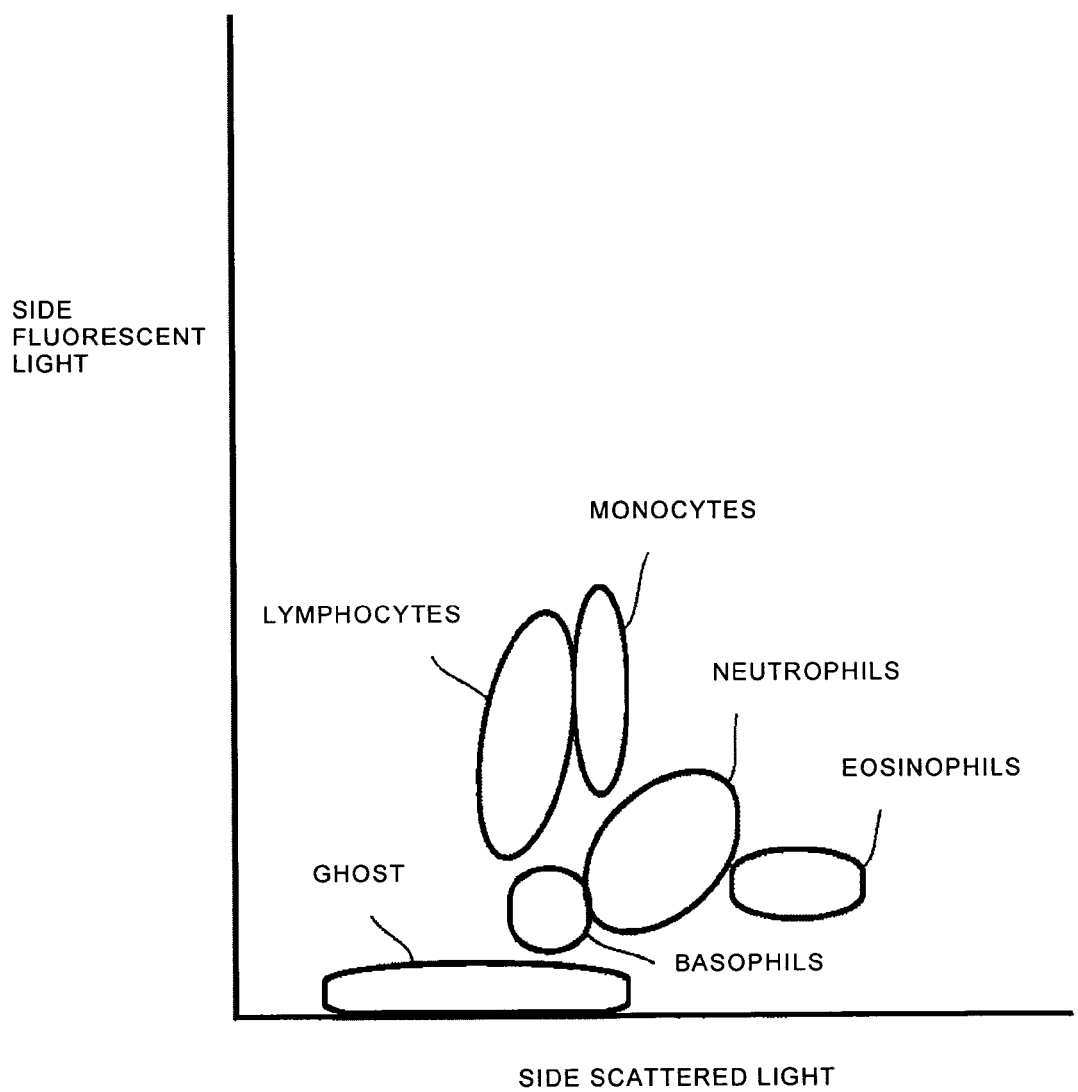
FIG. 14 is a scattergram obtained when the maximum allowable level of noise is set to 150 mVp-p.
Figure 15:
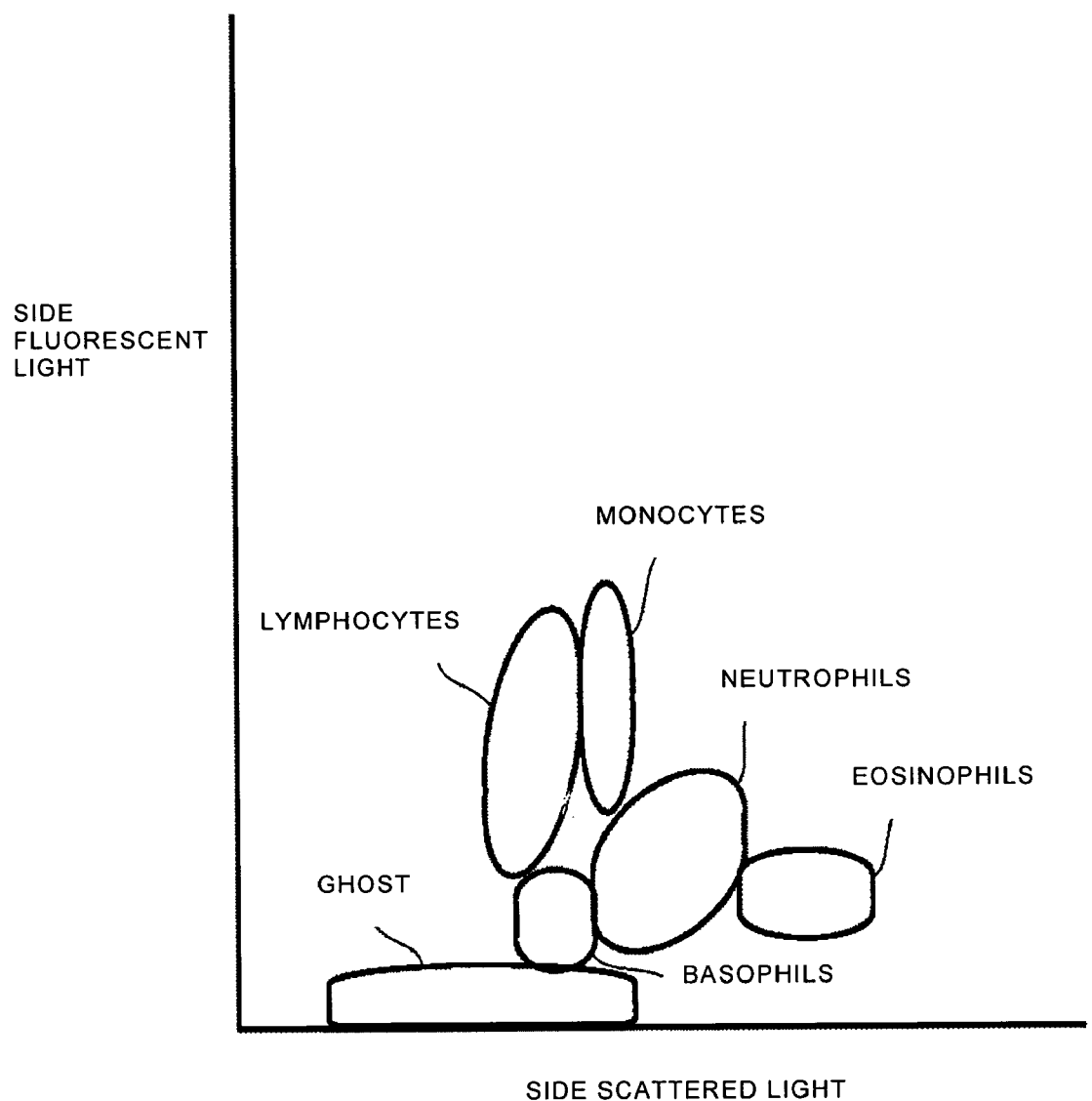
FIG. 15 is a scattergram obtained when the maximum allowable level of noise is set to 200 mVp-p.
Figure 16:
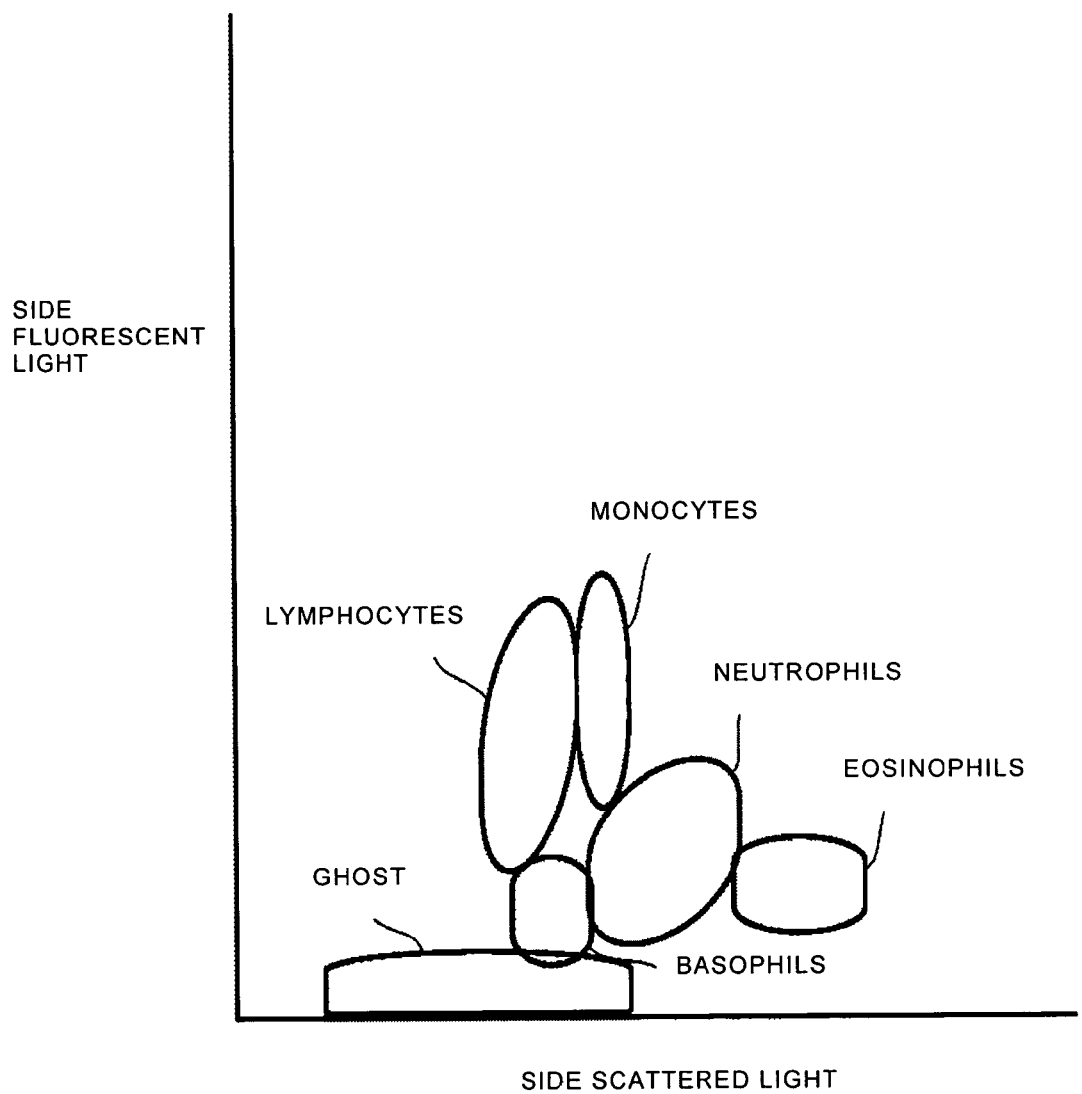
FIG. 16 is a scattergram obtained when the maximum allowable level of noise is set to 250 mVp-p.
Figure 17:
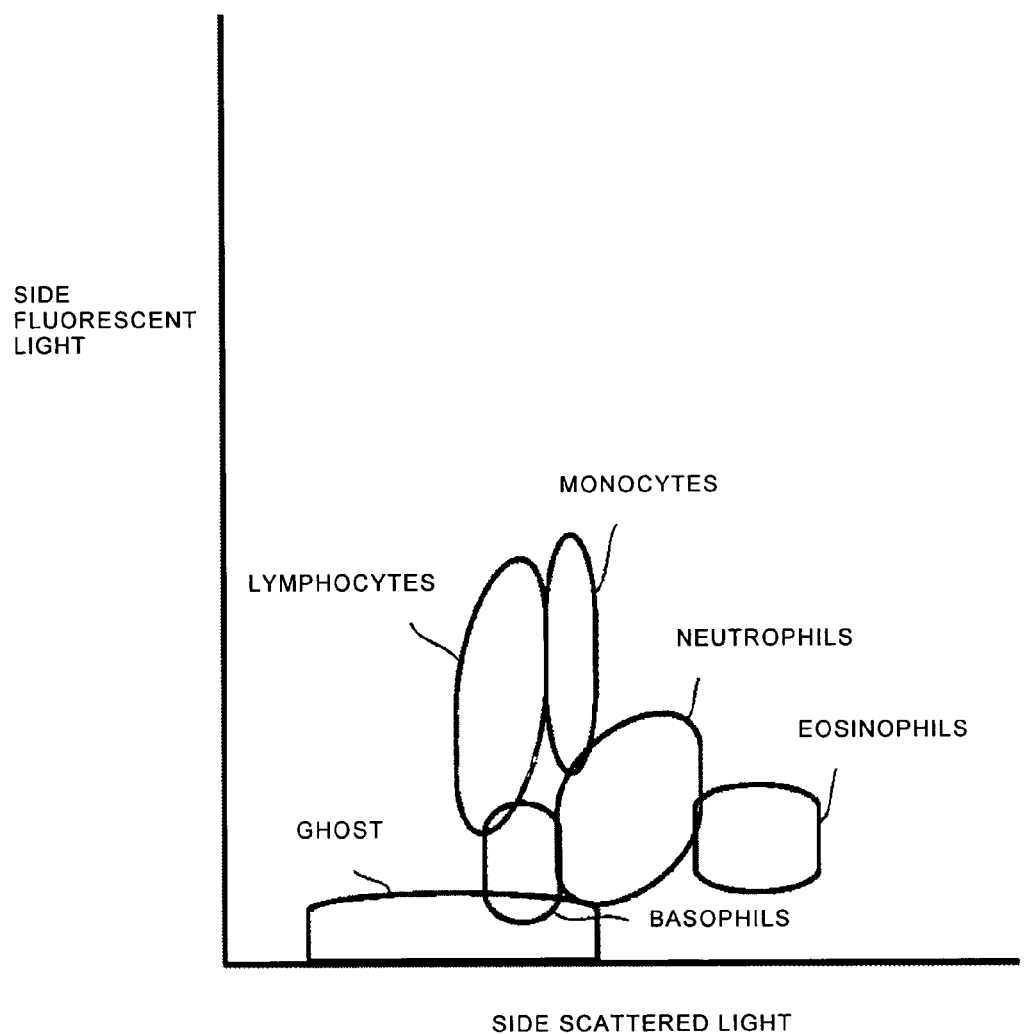
FIG. 17 is a scattergram obtained when the maximum allowable level of noise is set to 300 mVp-p.
Figure 18:
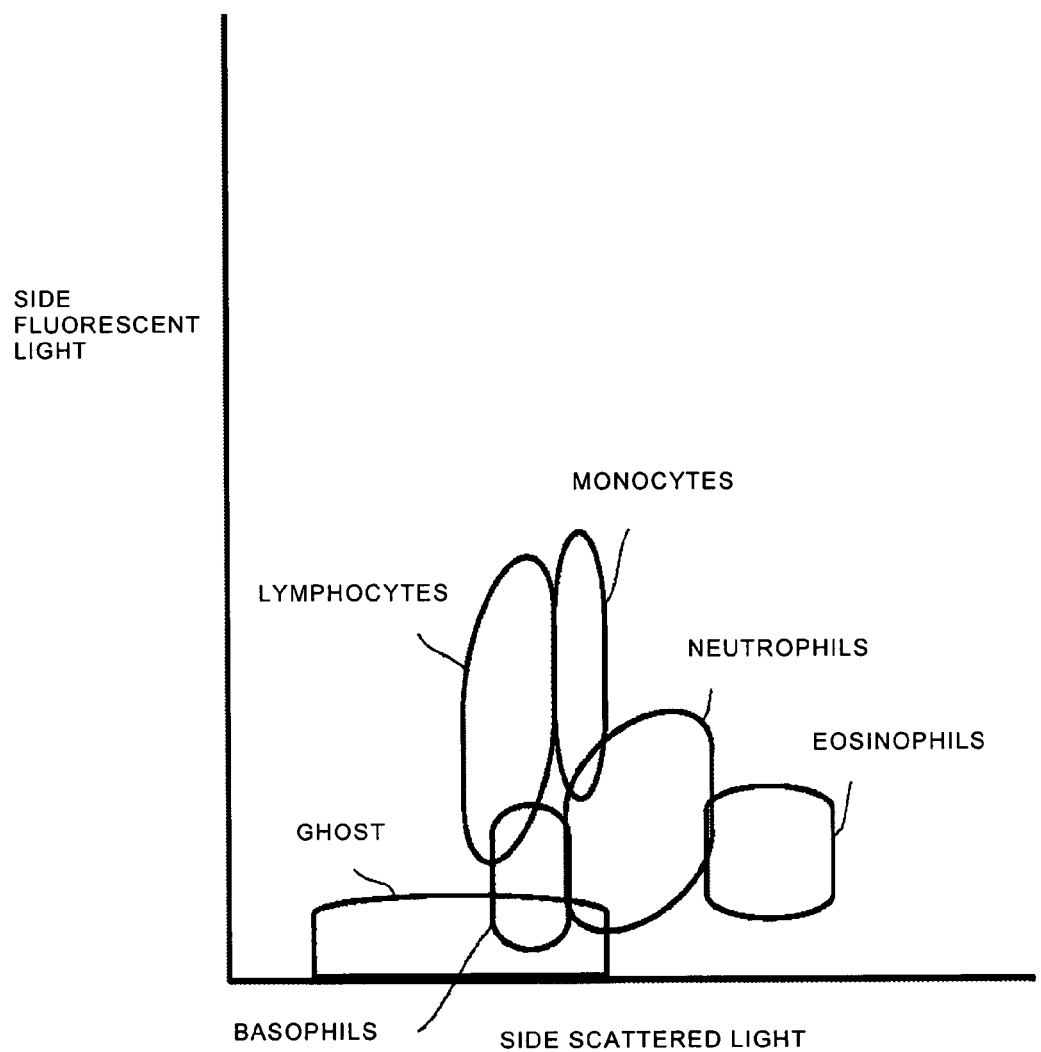
FIG. 18 is a scattergram obtained when the maximum allowable level of noise is set to 400 mVp-p.

This is based on the following knowledge of the inventors of the present invention. FIG. 11 is a frame format view explaining the range used in the analysis of the amplified signal of the side fluorescent light signal. As shown in FIG. 11, the full scale input voltage of the AD converter 83a is 4V, and the resolution is 8 bits in the blood analyzer 1 according to the present embodiment. The resolution on the vertical axis of the scattergram for white blood cell classification described above is 250 where the top six stages out of the data of 256 stages obtained from the output of the AD converter 83a are excluded. That is, the range using the output voltage of the amplifier 81a in the analysis of the data processing unit 3 is 250×4000/256=3906.25 mV. The inventors of the present invention performed experiments with a plurality of high pass cut-off frequencies of the low pass filter 84a set in the above condition, and researched to what extent the maximum allowable level of the noise contained in the signal after the noise reduction by the low pass filter 84a should be set to obtain a satisfactory analysis result. FIGS. 12 to 21 are scattergrams obtained for when the maximum allowable level is 80 mV-p, 100 mVp-p, 150 mVp-p, 200 mVp-p, 250 mVp-p, 300 mVp-p, 400 mVp-p, 500 mVp-p, 600 mVp-p and 700 mVp-p. In FIGS. 12 to 21, the regions enclosed with a solid line respectively show the respective regions in which neutrophils, lymphocytes, monocytes, eosinophils, and basophils are present. When the level of noise is 300 mVp-p, the overlap of the regions in which neutrophils, lymphocytes, monocytes, eosinophils, and basophils are present is small, and the white blood cells can be satisfactorily classified into five classifications with the noise level of such extent. In other words, an extremely satisfactory analysis is possible if the maximum allowable level of the noise contained in the amplified voltage is less than or equal to about 8% (100×300/3906.25=7.68%) with respect to the range (3906.25 mV) using the output voltage (amplified voltage) of the amplifier 81a in the analysis of the data processing unit 3.

Figure 19:
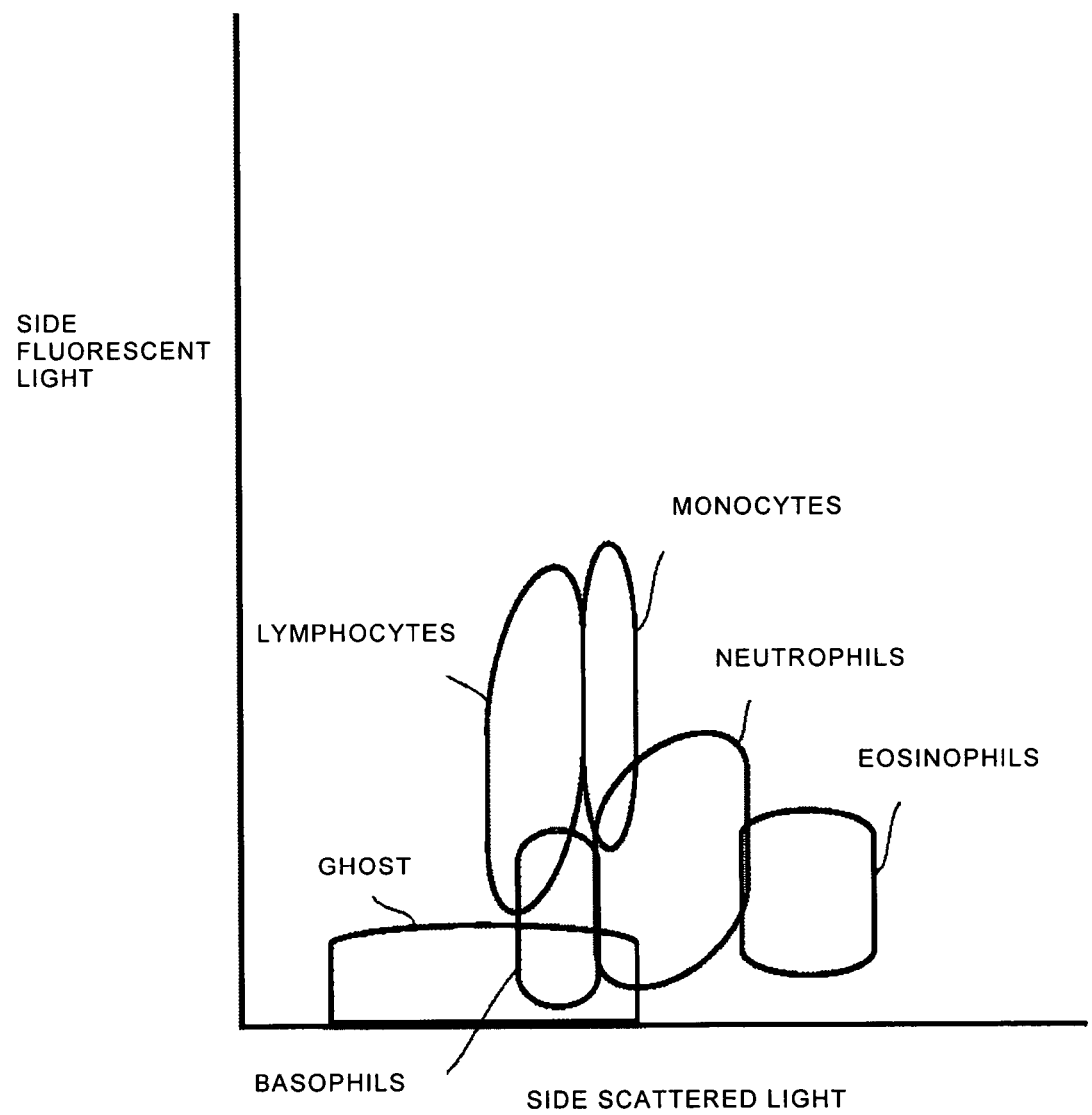
FIG. 19 is a scattergram obtained when the maximum allowable level of noise is set to 500 mVp-p.
Figure 20:
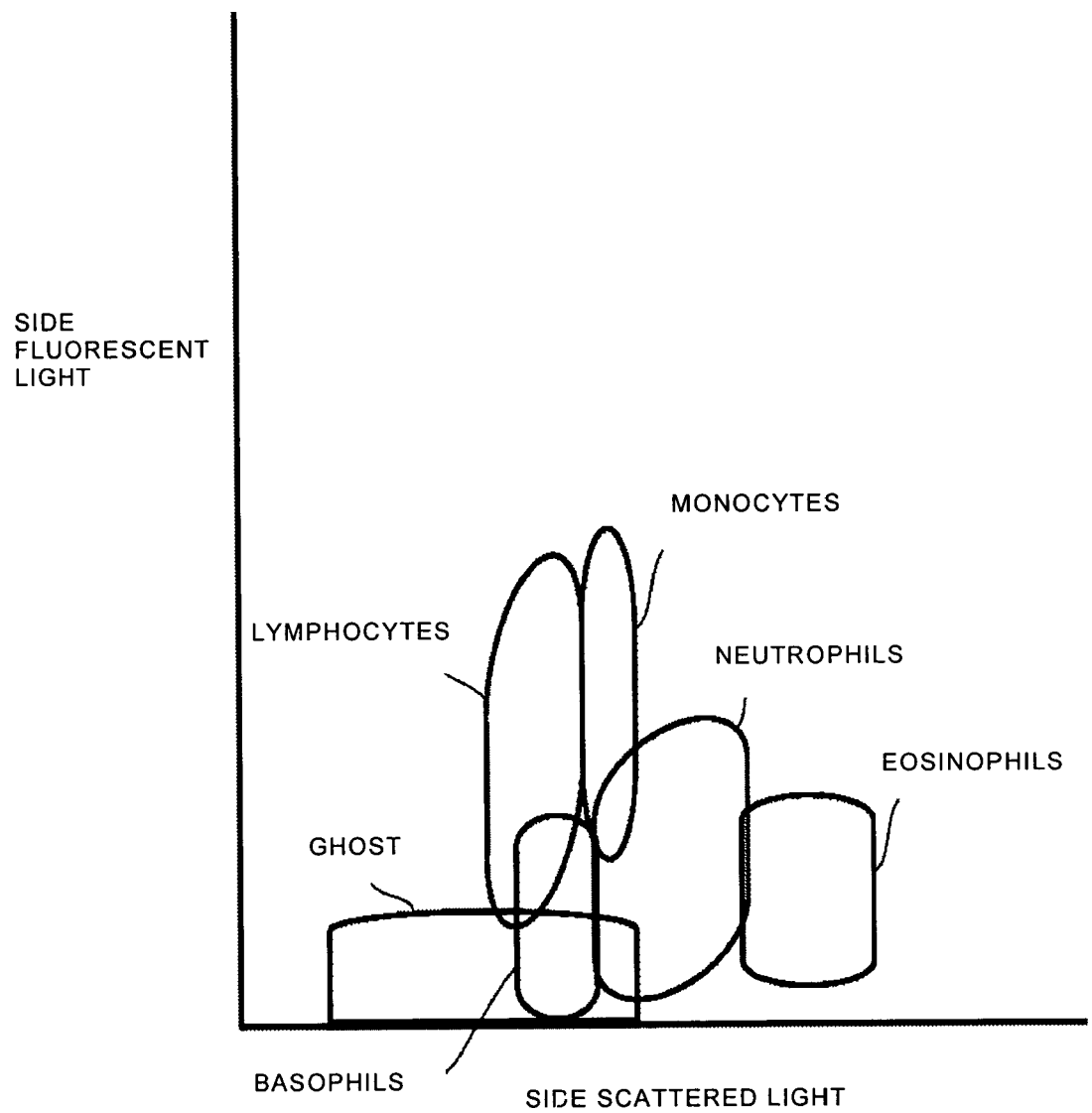
FIG. 20 is a scattergram obtained when the maximum allowable level of noise is set to 600 mVp-p.
Figure 21:
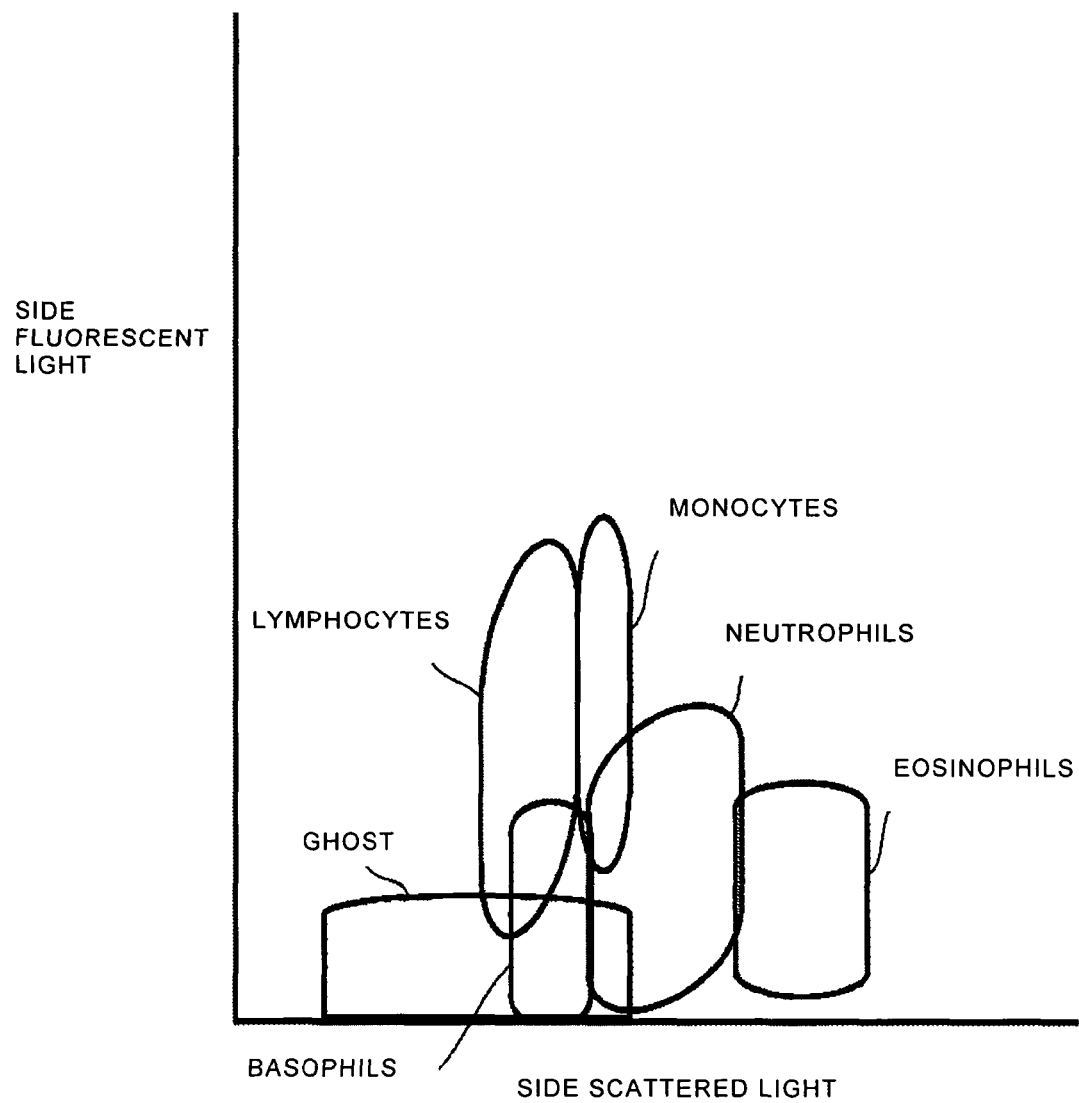
FIG. 21 is a scattergram obtained when the maximum allowable level of noise is set to 700 mVp-p.

The region in which the lymphocytes are present overlaps the region in which the ghosts are present, as shown in FIGS. 20 and 21, when the maximum allowable level of noise is greater than or equal to 600 mVp-p, but the region in which the lymphocytes are present and the region in which the ghosts are present do not overlap for 500 mVp-p, as shown in FIG. 19. High stainability is ensured while damaging the white blood cells to an appropriate extent and maintaining the form of the white blood cells with hemolytic agent in which the hemolyzing ability is not very high such as stromatolyser 4DS and stromatolyser 4DL, but the region in which the ghosts are present and the region in which the lymphocytes are present overlap and cannot be satisfactorily discriminated only with the side scattered light since the dissolving extent of the red blood cells is low. Therefore, in the classification of the white blood cells, accurate discrimination of the relevant lymphocytes and the ghosts is particularly important, and the respective appearing positions in the side fluorescent light intensity desirably do not overlap in order to discriminate the lymphocytes and the ghosts at high precision using the side fluorescent light intensity. From such standpoints, the position at which the lymphocytes are present and the position at which the ghosts are present do not overlap and can be satisfactorily discriminated when the maximum allowable noise level is less than or equal to 500 mVp-p, and the white blood cells can be satisfactorily classified as a result. Furthermore, the number of basophils is usually less than or equal to 1% of the entire white blood cells, and thus the fractionation of the basophils may not be performed since it is sufficiently practicable if the white blood cells can be classified into four classifications of neutrophils, lymphocytes, monocytes, and eosinophils. Moreover, the white blood cells may be classified into four classifications, the basophils may be independently measured, and the results may be combined to have five classifications. In this aspect as well, the overlap of the respective regions in which the neutrophils, lymphocytes, monocytes, and eosinophils are present is few, and the white blood cells can be satisfactorily classified into four classifications if the noise level is less than or equal to 500 mVp-p, as shown in FIG. 19. Therefore, satisfactory analysis is possible even if the maximum allowable level of the noise contained in the amplified voltage is less than or equal to about 13% (100×500/3906.25=12.8%) with respect to the usage range of the amplified voltage in the analysis of the data processing unit 3.

The avalanche photodiode has a property in that the inter-terminal capacity becomes larger and the S/N ratio of the output signal becomes lower as the light receiving surface becomes larger. Therefore, the noise component contained in the side fluorescent light signal increases as the light receiving surface of the avalanche photodiode becomes larger, whereby the high pass cut-off frequency of the low pass filter 84a must be set low. In other words, the high pass cut-off frequency corresponding to the maximum allowable level of the same noise changes according to the inter-terminal capacity of the avalanche photodiode.

Figure 22:
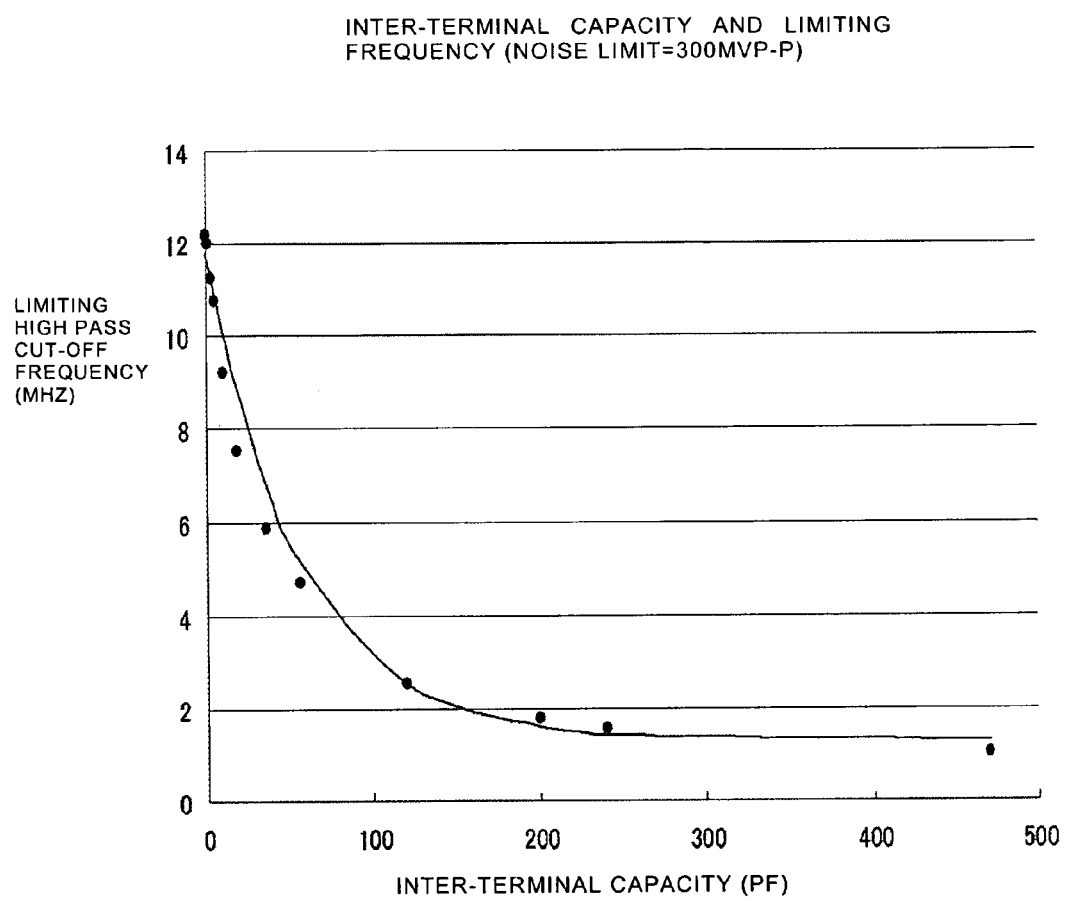
FIG. 22 is a graph showing the relationship between the inter-terminal capacity of the avalanche photodiode and the high pass cut-off frequency of the A/D converter when the maximum allowable level of noise is set to 300 mVp-p.
Figure 23:
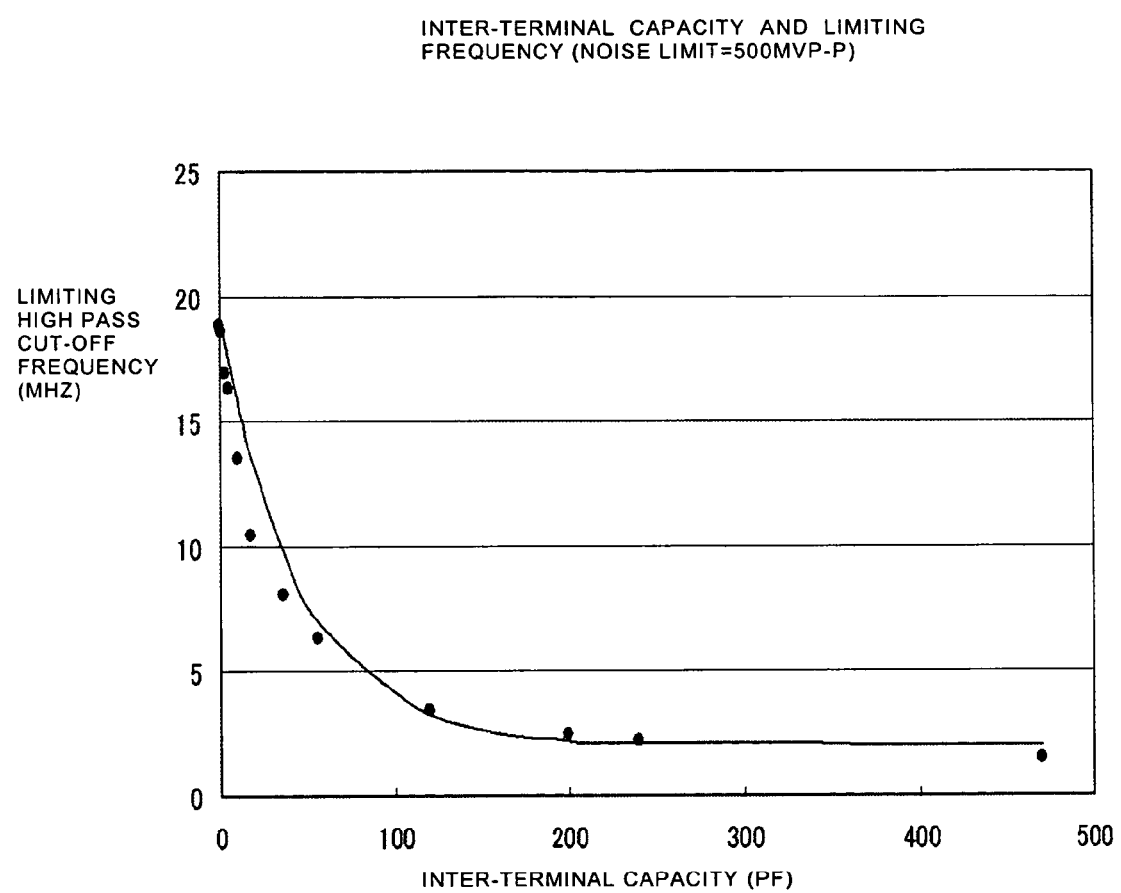
FIG. 23 is a graph showing the relationship between the inter-terminal capacity of the avalanche photodiode and the high pass cut-off frequency of the A/D converter when the maximum allowable level of noise is set to 500 mVp-p.

FIGS. 22 and 23 are graphs showing the relationship between the inter-terminal capacity of the avalanche photodiode and the high pass cut-off frequency of the low pass filter 84a of when the maximum allowable level of the noise is 300 mVp-p and 500 mVp-p, respectively. As a result of the experiment, the high pass cut-off frequency corresponding to the maximum allowable level of the noise of 300 mVp-p when the inter-terminal capacity is 0 pF was 10.28 MHz, as shown in FIG. 22. Similarly, when the maximum allowable level of the noise is 300 mVp-p, if the inter-terminal capacity is 1 pF, 3 pF, 5 pF, 10 pF, 18 pF, 36 pF, 56 pF, 120 pF, 240 pF, and 470 pF, the respective high pass cut-off frequency was 10.11 MHz, 9.6 MHz, 9.14 MHz, 7.97 MHz, 6.62 MHz, 5.19 MHz, 4.18 MHz, 2.22 MHz, 1.55 MHz, 1.35 MHz, and 0.87 MHz. The approximate expression of the relationship between the inter-terminal capacity and the limiting frequency of when the maximum allowable level of the noise is 300 mVp-p is as expressed with equation (5). In FIG. 22, the curve of equation (5) is shown with a solid line. On the other hand, when the maximum allowable level of the noise is set to 500 mVp-p, if the inter-terminal capacity is 0 pF, 1 pF, 3 pF, 5 pF, 10 pF, 18 pF, 36 pF, 56 pF, 120 pF, 240 pF, and 470 pF, the respective high pass cut-off frequency was 18.86 MHz, 18.62 MHz, 16.94 MHz, 16.35 MHz, 13.47 MHz, 10.48 MHz, 8.09 MHz, 6.32 MHz, 3.46 MHz, 2.47 MHz, 2.18 MHz, and 1.52 MHz, as shown in FIG. 23. The approximate expression of the relationship between the inter-terminal capacity and the limiting frequency of when the maximum allowable level of the noise is 500 mVp-p is as expressed with equation (6). In FIG. 23, the curve of equation (6) is shown with a solid line.

$$Y=17.289 EXP(-0.022C)+2 \quad \text{(eq.6)}$$

C: inter-terminal capacity of-avalanche photodiode

Therefore, the high pass cut-off frequency is set to lower than or equal to the frequency Y provided by equation (5) and the noise level contained in the signal after the noise reduction by the low pass filter 84a is set to less than or equal to 300 mVp-p in the present embodiment, but are not limited thereto, and the high pass cut-off frequency may be set to less than or equal to the frequency Y provided by equation (6), and the noise level to lower than or equal to 500 mVp-p, in which case, a satisfactory analysis result is also obtained. In particular, when classifying the white blood cells into four classifications, sufficient precision of analysis can be obtained even if the noise level is set to lower than or equal to 500 mVp-p.

As described above, the noise contained in the output signal can be further reduced by having a smaller inter-terminal capacity of the avalanche photodiode 58. The S/N ratio is enhanced by enhancing the intensity of the light emitted from the semiconductor laser light source 52, but such effect is low compared to when the light receiving surface (i.e., inter-terminal capacity) of the avalanche photodiode 58 is made small, and is also not preferable in terms of power consumption since the energy consumption increases when the level of the output light is increased. It is essential to have the light receiving surface of the avalanche photodiode 58 as small as possible. On the other hand, the light receiving surface may become smaller than the image of the particles projected onto the light receiving surface of the avalanche photodiode 58 by the side light collective lens 55 if the light receiving surface of the avalanche photodiode 58 is made small in excess, and the side fluorescent light signal accurately reflecting the information related to the particles may not be obtained. The image of the particles may be made smaller than the light receiving surface by reducing the magnification of the side light collective lens 55. However, if the light receiving surface is too small, the positional adjustment with the optical axis becomes difficult and high precision in assembly becomes necessary, which leads to increase in the manufacturing cost. Thus, the avalanche photodiode 58 having a circular light receiving surface of a diameter of 1.5 mm is used in the present invention taking into consideration the noise level of the output signal of the avalanche photodiode, the manufacturing cost of the optical lens, the precision in assembly of the WBC detection unit 5 and the like. The inter-terminal capacity of the avalanche photodiode 58 was 8.4 pF. The high pass cut-off frequency of the low pass filter 84a was 2.3 MHz in the present embodiment.

Although the shape of the light receiving surface of the avalanche photodiode 58 is circular with a diameter of 1.5 mm in the present embodiment, the shape is not limited thereto, and may be a circular shape with a diameter of 0.1 mm-2 mm, may be a square with a side length of 0.1-2 mm, or may be other shapes such as a rectangular shape having a surface area of the same degree.

Furthermore, the measurement unit 2 and the data processing unit 3 are separately arranged, the blood analyzer 1 is configured by such units in the present embodiment, but configuration of the blood analyzer 1 is not limited thereto, and an integrated blood analyzer having both the function of the measurement unit 2 and the function of the data processing unit 3 may be provided.

What is claimed is:

1. A blood analyzer, comprising:
a sample preparing part comprising a first chamber for preparing a first measurement sample comprising blood, a hemolyzing reagent, and a staining reagent and a second chamber for preparing a second measurement sample comprising blood and a diluent;
a first detection unit comprising a flow cell in which the first measurement sample flows, a light source for irradiating the first measurement sample flowing in the flow cell, a PIN photodiode for detecting a side scattered light from the first measurement sample irradiated by the light source, and an avalanche photodiode for detecting a side fluorescence light from the first measurement sample irradiated by the light source;
a second detection unit comprising a second flow cell in which the second measurement sample flows and electrodes that detect changes of direct current resistance therebetween caused by the second measurement sample flowing therebetween;
a signal processing part configured for processing a side scattered light signal from the PIN photodiode, a side fluorescent light signal from the avalanche photodiode and a third detection signal from the electrodes, the signal processing part comprising:
- gain-adjustable amplifiers configured to amplify the side scattered light signal and the side fluorescent light signal respectively at gains adjustable according to measurement modes, including a white blood cell classifying mode and a reticular red blood cell measurement mode;
- low pass filters configured to reduce high frequency noise included in the side scattered light signal and the side fluorescent light signal amplified by the gain-adjustable amplifier wherein;
- high pass filters configured to reduce fluctuations of base lines of the side scattered light signal and the side fluorescent light signal filtered by the low pass filters; and
- base line adjusters configured to adjust the base lines of the side scattered light signal and the side fluorescent light signal filtered by the high pass filters to a predetermined level; and
- an analysis part configured for classifying white blood cells in the first measurement sample into at least four groups, comprising neutrophils, lymphocytes, monocytes, and eosinophils, based solely on the side scattered light signal and the side fluorescent light signal processed by the signal processing part, and for counting red blood cells in the second measurement sample based on the third detection signal processed by the signal processing part.

2. The blood analyzer according to claim 1, wherein the analysis part classifies the white blood cells into neutrophils, lymphocytes, monocytes, eosinophils, and basophils.

3. The blood analyzer according to claim 1, wherein the low pass filter filtering the side fluorescent light signal reduces the high frequency noise to less than 13% of a using range of signal level of the side fluorescent light signal amplified by the gain-adjustable amplifier.

4. The blood analyzer according to claim 1, wherein the low pass filter filtering the side fluorescent light signal reduces the high frequency noise to less than 8% of a using range of signal level of the side fluorescent light signal amplified by the gain-adjustable amplifier.

5. The blood analyzer according to claim 1, wherein the avalanche photo diode comprises a light detecting round surface having diameter of between about 0.1 mm and about 2 mm.

6. The blood analyzer according to claim 1, wherein the avalanche photo diode comprises a light detecting rectangle surface having sides of between about 0.1 mm and about 2 mm.

7. The blood analyzer according to claim 1, wherein the light source comprises a laser diode.

8. The blood analyzer according to claim 7, wherein the laser diode irradiates red light.

9. The blood analyzer according to claim 1 wherein a cutoff frequency of the low pass filter is less than or equal to frequency Y of following formula:

$$Y=17.289 \text{EXP}(-0.022C)+2$$

wherein C represents electric capacity between terminals of the avalanche photo diode.

10. The blood analyzer according to claim 1, wherein a cutoff frequency of the low pass filter is less than or equal to frequency Y of following formula:

$$Y=10.482 \text{EXP}(-0.018C)+1.3$$

wherein C represents electric capacity between terminals of the avalanche photo diode.

11. A blood analyzing method, comprising:
- preparing a first measurement sample comprising blood, a hemolyzing reagent, and a staining reagent;
- preparing a second measurement sample comprising blood and a diluent;
- flowing the first measurement sample through a first flow cell and exposing the first measurement sample flowing through the first flow cell to light from a light source;
- detecting, by a PIN phtodiode, a side scattered light from the first measurement sample irradiated by the light source to thereby output a side scattered light signal from the PIN photodiode;
- detecting, by an avalanche photodiode, a side fluorescence light from the first measurement sample irradiated by the light source to thereby output a side fluorescent light signal from the avalanche photodiode;
- flowing the second measurement sample through a second flow cell;
- applying a direct current with electrodes to the second measurement sample flowing through the second flow cell and detecting a direct current resistance of the second measurement sample to thereby output a third detection signal from the electrodes;
- amplifying by gain-adjustable amplifiers the side scattered light signal and the side fluorescent light signal respectively at gains adjustable according to measurement modes, including a white blood cell classifying mode and a reticular red blood cell measurement mode;
- reducing by low pass filters high frequency noises included in the side scattered light signal and the side fluorescent light signal amplified by the gain-adjustable amplifiers;
- reducing by high pass filters fluctuations of base lines of the side scattered light signal and the side fluorescent light signal filtered by the low pass filters;
- adjusting by base line adjusters the base lines of the side scattered light signal and the side fluorescent light signal filtered by the high pass filters to a predetermined level;
- classifying white blood cells in the first measurement sample into at least four groups, comprising neutrophils, lymphocytes, monocytes, and eosinophils, based solely on the side scattered light signal and the side fluorescent light signal; and
- counting red blood cells in the second measurement sample based on the processed third detection signal.

12. The blood analyzing method according to claim 11, wherein the white blood cells are classified into neutrophils, lymphocytes, monocytes, eosinophils, and basophils.

* * * * *

UNITED STATES PATENT AND TRADEMARK OFFICE
CERTIFICATE OF CORRECTION

| | |
|---|---|
| PATENT NO. | : 7,916,280 B2 |
| APPLICATION NO. | : 11/599910 |
| DATED | : March 29, 2011 |
| INVENTOR(S) | : Kunio Ueno et al. |

It is certified that error appears in the above-identified patent and that said Letters Patent is hereby corrected as shown below:

In column 13, claim 1, line 13, replace "amplifier wherein;" with --amplifier;--.

In column 14, claim 11, line 18, after "detecting, by a PIN" replace "phtodiode" with --photodiode--.

Signed and Sealed this
Fourteenth Day of February, 2012

David J. Kappos
*Director of the United States Patent and Trademark Office*